United States Patent
Bergquist et al.

(10) Patent No.: US 10,053,258 B2
(45) Date of Patent: Aug. 21, 2018

(54) PACKAGING SCHEME FOR A PLURALITY OF CONSUMER GOODS

(71) Applicant: Edgewell Personal Care Brands, LLC, Chesterfield, MO (US)

(72) Inventors: Ilona Bergquist, Southport, CT (US); Sezen Buell, Waldwick, NJ (US); Ricardo de Oliveira, New Hope, PA (US); Anna Dietrich, Stamford, CT (US); Danielle Kay Gerlach, Fort Lee, NJ (US); Adebimpe Ogunade, Saddle Brook, NJ (US); Richard Timmers, Saddle Brook, NJ (US); Pankaj Nigam, Ridgewood, NJ (US); Kyle Hillegass, Milltown, NJ (US); Robert F. Rosasco, III, Woodbridge, CT (US)

(73) Assignee: Edgewell Personal Care Brands, LLC., Chesterfield, MO (US)

( * ) Notice: Subject to any disclaimer, the term of this patent is extended or adjusted under 35 U.S.C. 154(b) by 38 days.

(21) Appl. No.: 14/962,341

(22) Filed: Dec. 8, 2015

(65) Prior Publication Data
US 2017/0158373 A1 Jun. 8, 2017

Related U.S. Application Data

(60) Provisional application No. 62/089,467, filed on Dec. 9, 2014.

(51) Int. Cl.
*B65D 85/00* (2006.01)
*B65D 5/42* (2006.01)
(Continued)

(52) U.S. Cl.
CPC ............ *B65D 5/4212* (2013.01); *A47F 7/00* (2013.01); *G09F 23/00* (2013.01); *B65D 2203/00* (2013.01)

(58) Field of Classification Search
CPC .... B65D 5/4212; B65D 2203/00; G09F 23/00
(Continued)

(56) References Cited

U.S. PATENT DOCUMENTS 5,501,365 A 3/1996 Richiger et al.
5,682,999 A 11/1997 Larson
(Continued)

FOREIGN PATENT DOCUMENTS

EP 0986996 * 3/2000

*Primary Examiner* — Luan K Bui

(57) ABSTRACT

A packaging scheme for identifying consumer goods affiliated with, made and/or sold by a company and/or brand. The packaging scheme provides for a first product and a second product where the first product and the second product are different products, and a first package containing the first product and a second package containing both the first product and the second product. A first visual cue and/or a first packaging construction cue are associated with the first product. A second visual cue and/or a second packaging construction cue are associated with the second product, such that the first package has a first visual cue and/or a first packaging construction cue, while the second package has both a (i) first visual cue and/or a first packaging construction cue, and (ii) a second visual cue and/or a second packaging construction cue.

19 Claims, 16 Drawing Sheets

(51) Int. Cl.
*A47F 7/00* (2006.01)
*G09F 23/00* (2006.01)

(58) Field of Classification Search
USPC ..... 206/440, 441, 459.5, 494, 570–572, 534
See application file for complete search history.

(56) References Cited

U.S. PATENT DOCUMENTS

| | | | |
|---|---|---|---|
| 5,725,382 A * | 3/1998 | Walter | A61F 13/551 |
| | | | 206/459.5 |
| 5,839,585 A | 11/1998 | Miller | |
| 5,865,322 A | 2/1999 | Miller | |
| 5,878,947 A | 3/1999 | Hoy et al. | |
| 5,947,302 A | 9/1999 | Miller | |
| 6,062,424 A | 5/2000 | Simile-Gravina et al. | |
| 6,093,027 A | 7/2000 | Unger et al. | |
| 6,123,222 A | 9/2000 | Richiger et al. | |
| 6,176,419 B1 | 1/2001 | Holley, Jr. | |
| 6,386,113 B1 | 4/2002 | Unger et al. | |
| 6,409,077 B1 | 6/2002 | Telesca et al. | |
| 6,454,095 B1 * | 9/2002 | Brisebois | A61F 13/551 |
| | | | 206/440 |
| 6,578,736 B2 | 6/2003 | Spivey | |
| 6,601,705 B2 | 8/2003 | Molina et al. | |
| 6,604,677 B1 | 8/2003 | Sutherland et al. | |
| 6,688,466 B2 | 2/2004 | White et al. | |
| 6,708,823 B2 | 3/2004 | Cottingham et al. | |
| 6,763,944 B2 * | 7/2004 | Ronn | A61F 13/84 |
| | | | 206/440 |
| 6,913,146 B2 | 7/2005 | Bechyne et al. | |
| 6,918,487 B2 | 7/2005 | Harrelson | |
| 6,923,321 B2 | 8/2005 | Samolinski et al. | |
| 6,929,172 B2 | 8/2005 | Bates et al. | |
| 6,948,616 B2 | 9/2005 | Gillani | |
| 7,000,803 B2 | 2/2006 | Zumbiel | |
| 7,048,308 B2 | 5/2006 | Blank | |
| 7,144,391 B1 | 12/2006 | Kreutz et al. | |
| 7,168,558 B2 | 1/2007 | Harrelson | |
| 7,172,073 B2 | 2/2007 | Hanson | |
| 7,178,671 B2 | 2/2007 | Nichols et al. | |
| 7,185,761 B2 * | 3/2007 | Molina | A61F 13/551 |
| | | | 206/440 |
| 7,370,760 B2 | 5/2008 | Clough | |
| 7,413,101 B2 | 8/2008 | Smalley et al. | |
| 7,422,106 B1 | 9/2008 | Kendra | |
| 7,487,906 B2 | 2/2009 | Molinare et al. | |
| 7,523,825 B2 | 4/2009 | Velazquez et al. | |
| 7,588,166 B2 | 9/2009 | McDaniel et al. | |
| 7,694,818 B2 | 4/2010 | Molina et al. | |
| 7,721,887 B2 | 5/2010 | Hancock-Cooke et al. | |
| 7,785,308 B2 | 8/2010 | Denti et al. | |
| 7,793,485 B2 | 9/2010 | Blocker | |
| 7,913,845 B2 | 3/2011 | Velazquez et al. | |
| 7,942,265 B2 | 5/2011 | Luzzatto et al. | |
| 7,946,420 B2 | 5/2011 | Molina et al. | |
| 7,950,522 B2 | 5/2011 | Slayton et al. | |
| 7,958,994 B2 | 6/2011 | Weinmann | |
| 8,006,833 B2 | 8/2011 | Clark, Jr. et al. | |
| 8,066,178 B2 | 11/2011 | Sorrentino | |
| 8,066,186 B2 | 11/2011 | Kidwell | |
| 8,074,801 B2 | 12/2011 | Slayton et al. | |
| 8,186,513 B2 | 5/2012 | John et al. | |
| 8,191,709 B2 | 5/2012 | Molina et al. | |
| 8,225,930 B2 | 7/2012 | Ruman | |
| 8,281,926 B2 | 10/2012 | Lambertus et al. | |
| 8,378,165 B2 * | 2/2013 | Visscher | A61F 13/55145 |
| | | | 604/361 |
| 8,386,326 B2 | 2/2013 | Woltman et al. | |
| 8,500,022 B2 | 8/2013 | Kidwell et al. | |
| 8,517,175 B2 | 8/2013 | Molina et al. | |
| 8,548,875 B2 | 10/2013 | Woltman et al. | |
| D700,450 S | 3/2014 | Glenn | |
| D708,962 S | 7/2014 | Glenn | |
| 8,793,163 B2 | 7/2014 | Woltman et al. | |
| D712,750 S | 9/2014 | Glenn | |
| D718,149 S | 11/2014 | Glenn | |
| 8,936,584 B2 | 1/2015 | Zander et al. | |
| 8,944,251 B1 | 4/2015 | Yecies et al. | |
| 9,242,775 B2 * | 1/2016 | Knobloch | B65D 71/00 |
| 2004/0102748 A1 * | 5/2004 | Hirotsu | A61F 13/551 |
| | | | 604/358 |
| 2006/0069372 A1 * | 3/2006 | Chakravarty | A61F 13/15617 |
| | | | 604/385.02 |
| 2007/0051726 A1 | 3/2007 | Arkins | |
| 2007/0245143 A1 | 3/2007 | Clough et al. | |
| 2007/0078417 A1 * | 4/2007 | Bohan | A61K 9/0031 |
| | | | 604/304 |
| 2007/0144929 A1 | 6/2007 | Minerath, III et al. | |
| 2007/0295629 A1 | 12/2007 | Adriaanse et al. | |
| 2009/0120816 A1 | 5/2009 | Ruman et al. | |
| 2009/0120825 A1 | 5/2009 | Ruman et al. | |
| 2009/0120834 A1 | 5/2009 | Ruman et al. | |
| 2009/0197231 A1 | 8/2009 | Sosalla | |
| 2010/0000897 A1 | 1/2010 | Bumpass et al. | |
| 2010/0193386 A1 | 8/2010 | Loyd et al. | |
| 2011/0094912 A1 | 4/2011 | Rossi et al. | |
| 2011/0132976 A1 | 6/2011 | Drewnowski et al. | |
| 2011/0139656 A1 * | 6/2011 | Nukuto | B65D 5/4204 |
| | | | 206/459.5 |
| 2012/0152784 A1 | 6/2012 | Nukuto et al. | |
| 2014/0034538 A1 | 2/2014 | Biggs et al. | |
| 2014/0131252 A1 | 5/2014 | Ruman | |
| 2014/0131253 A1 | 5/2014 | Ruman | |
| 2014/0155810 A1 | 6/2014 | Buell et al. | |
| 2014/0312049 A1 | 10/2014 | Glenn | |
| 2014/0343910 A1 | 11/2014 | Zheng et al. | |
| 2014/0348444 A1 | 11/2014 | Puccini | |
| 2014/0348445 A1 | 11/2014 | Cassanova et al. | |
| 2015/0041362 A1 | 2/2015 | Ruman | |

* cited by examiner

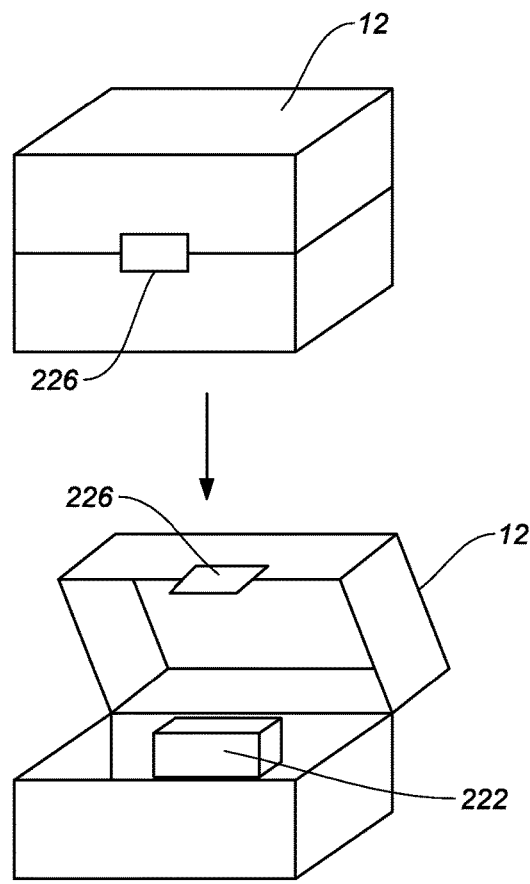
FIG. 29
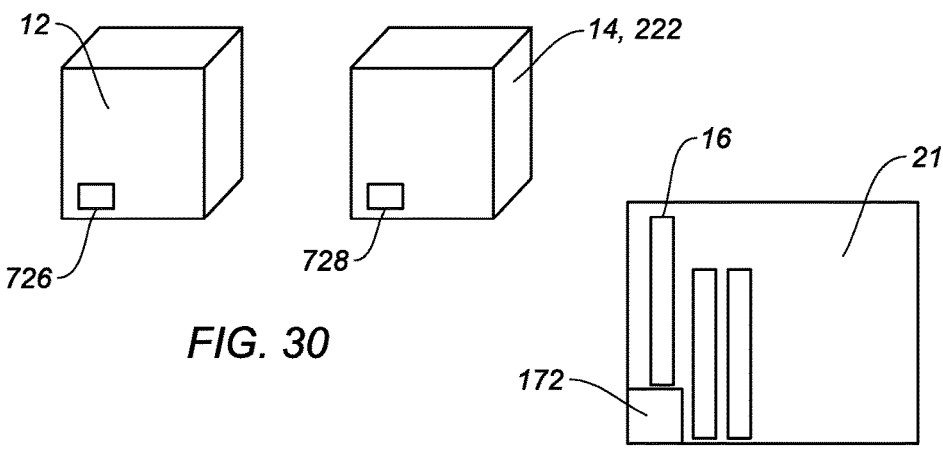
FIG. 30
FIG. 31

PACKAGING SCHEME FOR A PLURALITY OF CONSUMER GOODS

CROSS-REFERENCE TO RELATED APPLICATIONS

This application claims priority to U.S. Provisional Patent Application No. 62/089,467, filed Dec. 9, 2014, the contents of which are incorporated herein.

BACKGROUND OF THE INVENTION

A. Field of Endeavor

The present disclosure is related to packaged consumer goods, and more particularly, to a packaging scheme for identifying particular types of goods within a plurality of goods affiliated with, made and/or sold by a company and/or brand.

B. Background Information

Consumer goods, including the likes of household, personal, sanitary, cleansing and grooming products such as but not limited to batteries, flashlights, gloves, wipes, tampons, sanitary napkins, pads and liners, diapers, incontinence devices, pessaries, razors, shaving preparations, infant and child care goods, pet care and pet waste removal goods, lotions, soaps, sunscreen, and tanning products, are commercially produced and sold to consumers with wrappers and/or in packaging. The package of consumer goods as it is offered to the consumer has a front facing panel which is displayed to a consumer and which includes any number of visual elements in a variety of arrangements to provide distinction between products, product tier levels or even product sub-brands. However, it has been found that many consumers today are confused and overwhelmed at the retail shelf when trying to locate a particular product amongst many different products, even when the products are of a single principal brand. This problem is further complicated by inconsistencies in the packaging schemes for each package. As such, consumers are unable to quickly browse the retail shelf to locate the desired product, the desired product brand, sub-brand, master brand, and/or combinations thereof. For example, package viewing area components, such as the current graphics utilized, the placement of such graphics, the fonts and font sizes of utilized, the colors utilized, and the general arrangements of such components can make sub-brand distinction, tier distinction, product benefits and the ability for a consumer to choose the right product to match a user's need, can make the shopping experience confusing and unclear. In addition, there are many inconsistencies across particular brand lines that do not add any further value to the seller and/or consumer, making the brand even more difficult to shop.

The retail shelf can be a further hindrance to the consumer who is looking not necessarily for a brand, sub-brand and/or master brand, but for the product itself. In packaging schemes where multiple products are offered, it can be difficult for the consumer to pick the right product and not merely a different product having the same branding and/or packaging scheme. Current packaging schemes provide visual information about the product to consumer but fail to tie at least one of a visual cue and a packaging construction cue to the type of product itself.

The retail shelf is further unforgiving to the consumer who is looking to alleviate multiple consumer and/or product needs with a single purchase. Consumers who are looking to purchase sanitary products such as those for personal grooming, incontinence and/or for feminine hygiene often times need more than one type of product (i.e. diapers and wipes, tampons and napkins, razors and pre and/or post shaving preparation, etc. . . . ). Further, a consumer seeking to satisfy one or more needs of more than one person within a single household is faced with the further difficulty of buying multiple different products. As many of these items can be located in different sections and/or organized differently, time, space in the shopping cart, and/or money becomes a limiting factor.

Retail can be further confusing to the consumer traveling amongst different countries and/or regions. Not only are stores organized differently in different regions/countries, different cultures that comprise a majority of a particular region or country can value products and/or attributes of a product that vary from cultures of a different region or country. Further, as some countries, regions and/or local authorities regulate products and/or govern consumer goods differently, packaging and advertising constraints can further limit what information about the product can be conveyed in a particular country or region. As such, packaging schemes amongst these different countries and/or regions will vary in order to flag and direct information that is meaningful to the attributes the consumer of that region values.

Consumers add yet another variable to the retail experience. As some consumers peruse shelves and walk through aisles with products, some consumers will pick-up items to examine them, only to place them back on the shelf such that the typical front facing panel is no longer noticeable and/or the product is placed back on the wrong shelf location.

In an age of mergers, acquisitions, and divestitures that are especially prevalent in consumer good companies such as those that manufacture and/or sell personal, grooming and/or sanitary products, the consumer is at risk of not knowing where a favorite brand and/or product went as it is merged and/or discontinued. This is particularly troublesome when two products that directly compete and/or compete in adjacencies become one organization. This concerning scenario is contrasted with an equally distressing consequence of mergers and acquisitions: how does a company communicate to the consumer that despite a different brand and/or sub-brand, the products are made/sold by the same parent company? Communicating this is delicate as certain consumers find comfort in this information, while other consumers would prefer to keep a brand and/or product isolated from other affiliated brands and/or products.

As technology has progressed and online retail has increased via computers (i.e. laptops, desk tops), tablets, notebooks and smart devices such as phones, PDA's, etc. . . . ), it is becoming increasingly important for consumers to be able to browse an electronic or digital retail shelf such as a webpage and being able to quickly determine what brand and/or what product something is by a somewhat small photograph and/or caption. While some websites, mobile sites and/or apps provide filtering means, not all websites a particular consumer good is advertised and/or sold on provide sufficient filtering means to actually narrow results to the product sought. Further, even if filtering has been successful, the consumer still needs to be able to quickly identify the brand and/or product from a somewhat small photograph of the product packaging.

Thus, there is a need for a packaging scheme that equips a consumer with the ability to quickly browse the retail shelf to locate one or more desired products. There is also a need for a packaging scheme amongst a company and/or principal brand distinguishing products, brands, sub-brands and/or product tiers. There is a further need for a system that equips a consumer with the ability to choose the right product to match one or more user's need(s) such as specific personal attributes, development stage(s), and/or level of symptoms. There is also a further need for a system that more clearly conveys the benefits of the products disposed within a corresponding package. There is a further need for a consumer goods packaging scheme that reduces the number of variables that can lead to a delayed and/or frustrating consumer purchasing experience. Further still, there is a need for a consumer goods packaging scheme that improves the consumer's ability to purchase necessary consumer goods by reducing the number and/or magnitude of limiting factors that affect the consumer's purchasing decisions. There is yet a further need for a consumer goods packaging scheme that enables particular global regions to tout product information in a way that is meaningful to its key consumer groups while also enabling the international consumer to find the product the consumer desires. Further still, another need exists for providing multiple products to a consumer in a single package. There is a further need to provide a packaging scheme having at least two products in a single package, where each individual product has at least one of a visual cue and packaging construction cue, where both product's schemes are on their respective individual packages and also the combination package.

Accordingly, there is a need for a packaging scheme and methods related thereto that overcome, alleviate, and/or mitigate one or more of the aforementioned deficiencies of prior art wrappers.

SUMMARY

The present disclosure provides a packaging scheme having at least two different packages. The first package has at least a first product, while the second package also has at least a first product and also at least a second product, the second product being different from the first product. The first package has a visual cue and/or packaging construction cue that is associated to the at least one first product. The second package has a first visual cue and/or packaging construction cue that relates directly to the first product, and a second visual cue and/or packaging construction cue that relates directly to the second product. The consumer can identify both the first package and the second package as having a packaging scheme.

In a further embodiment, the packaging scheme also has at least a third package that is different from the first and second packages. The third package also has at least the second product. The third package has a visual and/or packaging construction cue that relates directly to the at least one second product.

In a further embodiment, the packaging scheme provides consistent elements across the at least two different packages. In one embodiment, a branding indicium has a visual, tactile, olfactory, and/or audible indicium that is consistent amongst the first and second packages. In a further embodiment, a sub-brand indicium has a visual, tactile, olfactory, and/or audible indicium that is consistent amongst the first and second packages. In some embodiments, the sub-brand indicium can have different visual, tactile, olfactory, and/or audible indicium such that the consumer is readily able to distinguish the different products contained in the first and second packages while also understanding that a product is related to any other products in the packaging scheme.

In a further embodiment, the packaging scheme provides further qualitative and/or quantitative indicium that has a consistent visual, tactile, olfactory, and/or audible indicium. In these embodiments, the consumer is readily able to distinguish features and/or information about the product(s) contained within the package while also understanding that this product is related to other products in the packaging scheme.

In a further embodiment, the at least one second package provides information to the consumer in a consistent way for both products. In one embodiment, the brand indicium and/or sub-brand indicium extends into at least one communication zone of the package that describe the at least one first product and the at least one second product. In another embodiment, the qualitative and/or quantitative indicium is provided with a consistent visual, tactile, olfactory, and/or audible indicium, and/or is further provided in a zone on the packaging that is symmetric with the information provided for the other product.

In a further embodiment, the at least one second package provides a visual and/or packaging indicium that corresponds to the qualitative and/or quantitative features of the product. In one embodiment, a visual indicium of the first product makes up at least one-half of at least a first principal communication zone of the package. In a further embodiment, a visual indicium of the second product makes up at least one-half of at least a first principal communication zone of the package. In another embodiment, the visual indicium of the first product makes up less than or equal to one half of at least a first principal communication zone of the package. In another embodiment, the percentage of the amount of space the visual indicium corresponding to the at least one first product correlates the quantity of the at least one first product contained within the package with respect the total number of products contained within the package. In yet another embodiment, the percentage of the amount of space the visual indicium corresponding to the at least one second product correlates to the quantity of the at least one second product contained within the package with respect to the total number of products contained within the package. In yet another embodiment, the percentage of the amount of space the visual indicium corresponding to the at least one first product correlates to the volume of space the first product contained within the package occupies with respect to the volume of space occupied by other products in the package. In yet a further embodiment, the percentage of the amount of space the visual indicium corresponding to the at least one second product correlates to the volume of space the second product contained within the package occupies with respect to the volume of space occupied by other products in the package. In any of the aforementioned embodiments, the visual indicium can be presented on the principal communication zone, a different communication zone, and/or combinations thereof such that the visual indicium comprises one or more communication zones and/or is repeated on each individual communication zone.

In yet a further embodiment, a packaging scheme is provided wherein at least one of the visual, audible, olfactory and/or tactile indicium extends into at least a second communication zone of the package that cannot be the principal communication zone a consumer can initially identify. In this and related embodiments, a packaging scheme is provided to alleviate one or more of the following problems: variant shelf space in brick and mortar retailers, the variant size of product information that appears on electronic devices, a consumer misplacing a package in a brick and mortar retail store such that the principal communication zone is no longer oriented properly and/or misplaces the package in the wrong product section or aisle, and/or a consumer virtually viewing the package information such that the principal communication zone is no longer presented on the electronic device and the indicium that cues the consumer to know what product and/or brand are obfuscated. In some embodiments, a visual, audible, olfactory, and/or tactile indicium extends completely around at least one periphery of the package. In further embodiments where the package has edges and/or corners that physically separate communication zones and/or panels of the package structure from each other, the visual, audible, olfactory, and/or tactile indicium extends onto one or more of the panels.

In yet another embodiment, a packaging construction cue is provided such that the structure of the package (such as the geometric configuration of the package itself, the material, the continuity and/or ports within the package, and/or the opaqueness or translucency of the package due in part to the material) corresponds to the specific consumer product. The packaging construction cue can assist the consumer in removing product from the package and/or can assist the consumer in identifying the contents of the package. In one embodiment, a first product scheme relates to a first consumer product, while a second product scheme relates to a second product. A first package has the first product scheme and at least partially contains the first product, while a second package is at least partially the first product scheme and at least partially the second product scheme; the second package at least partially contains the first product and at least partially contains the second product. In further embodiments, a third package has the second product scheme and at least partially contains the second product. The first package, second package and optionally the third package all have a packaging scheme.

In yet another embodiment, a packaging scheme is provided such that packaging appealing to a first set of consumers is maintained while also corresponding in at least one regard to other packaging that appeals to a second set of consumers. In one embodiment, the first set of consumers is in a first global region while a second set of consumer is in a second global region. In another embodiment, the first set of consumers is a first consumer demographic while the second set of consumers is a second consumer demographic. In another embodiment, the packaging scheme provides at least one of a visual, tactile, olfactory and/or audible indicium that is consistent amongst both the first set and second set of consumer groups.

In yet a further embodiment, a packaging scheme is provided such that the at least one first product has a packaging construction cue that exudes the essence of, characteristics of, or an emotional state reflective of the product, and/or the target demographic. In one embodiment, the product is feminine care product and the packaging scheme includes gracious and elegant curves, where some of such curves are packaging construction cues.

BRIEF DESCRIPTION OF THE SEVERAL VIEWS OF THE DRAWINGS

The foregoing and other features, aspects and advantages of the present disclosure will become better apparent with regard to the following description, appended claims and accompanying drawings where:

FIG. 29 is a representation of an embodiment of a package FIG. 30 is a representation of an embodiment of a package FIG. 31 is a representation of an embodiment of a package

DETAILED DESCRIPTION OF THE INVENTION

Figure 1:
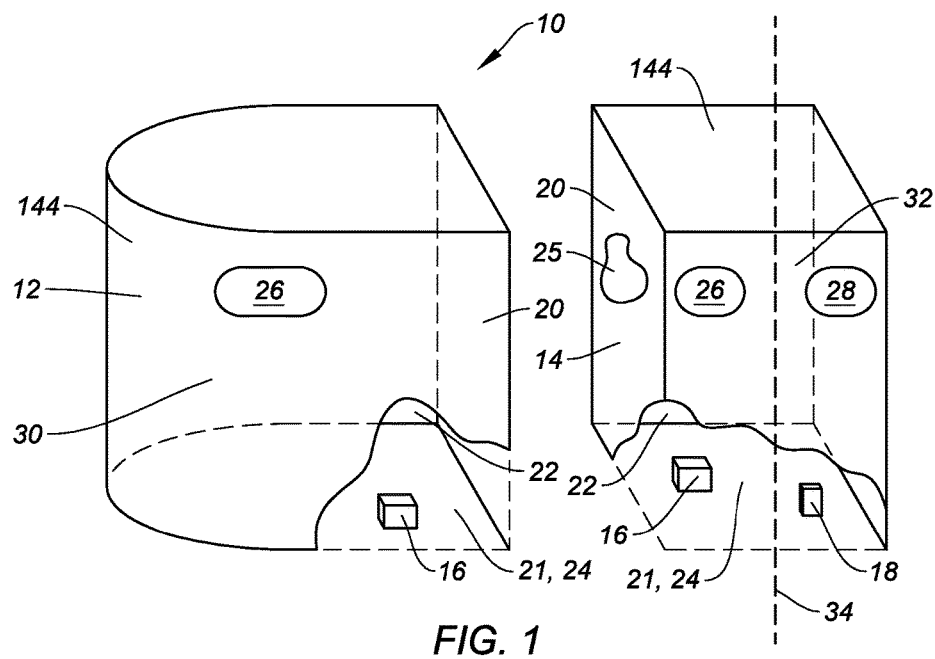
FIG. 1 is a representation of an embodiment of a packaging scheme

The present disclosure will be discussed hereinafter in detail in terms of the preferred embodiments according to the present disclosure with reference to the accompanying drawings. In the following description, numerous, specific details are set forth in order to provide a thorough understanding of the present disclosure. It will be obvious, however, to those skilled in the art that the present disclosure can be practiced without these specific details. In other instances, well-known structures are not shown in detail in order to avoid unnecessary obscurity of the present disclosure.

As used herein, the term "consumer products" refers to products that assist consumers in their lives such as goods used for hygiene, household products, simplification or improvement of activities, and sustenance, such as, personal, sanitary and/or grooming products. As used herein, the terms "products", "goods" and "consumer goods" are to be synonymous with "consumer products".

As used herein, the term "personal products" are used for hygiene, simplification or improvement activities and sustenance such as sanitary, grooming and/or other products including without limitation: sunscreen, tanning infant care and child care products.

As used herein, the term "sanitary products" refers to products that assist in cleansing and/or assisting with bodily functions such as gauze, swabs, cotton balls/pads, diapers, napkins, tampons, pessaries, suppositories, incontinence devices, and wipes.

As used herein, the term "grooming products" refers to products that assist in grooming the body such as shaving preparations such as gels, foams, crémes and lotions, razors, and other accoutrements used for personal grooming.

As used herein, the term "packaging scheme" refers to an overall scheme of the package as it relates to one or more consumer products that a manufacturer, seller, and/or a retailer wish to correlate to the consumer. For purposes of the present disclosure, the terms "associate" and "correlate" are synonymous and are to be used interchangeably.

As used herein, the term "product scheme" refers to the packaging scheme for a particular product. The product scheme is consistent with the packaging scheme in at least one regard (i.e. at least one attribute is shared with at least one other package in the packaging scheme). The product scheme can differ from the packaging scheme in at least one regard (i.e. at least one attribute is different from other packages amongst the packaging scheme).

As used herein, the terms "attribute" and "characteristic" refer to anything that provides information about the product, or any feature, indicium or cue that is associated with the product. For purposes of the present disclosure, the terms "attribute" and "characteristic" are synonymous and are to be used interchangeably.

As used herein, the term "communication zone" refers to an area of the package that provides information to the consumer via a visual cue, a packaging construction cue, visual, tactile, olfactory and/or audible indicium.

As used herein, the term "principal communication zone" refers to an area of the package that is typically the first area of a package that might be apparent to the consumer while shopping.

As used herein the term "visual cue" refers to how information is provided on the package such that the consumer can easily identify information about a particular product within the package. Visual cue can include other sensory cues such as tactile, olfactory and audible indicium.

As used herein, the term "packaging construction cue" refers to the structure of the package such as the geometric configuration of the package itself, the material, the continuity, openings, ports and/or windows within the package, and/or the opaqueness or translucency of the package due in part to the material. A packaging construction cue corresponds to a specific consumer product. A packaging construction cue can assist the consumer in removing a product from the package and/or can assist the consumer in identifying the contents of a package. One package at least partially containing at least two different consumer products can have a packaging construction cue for each of the at least two products. For purposes of the present disclosure, the term "opening" refers to an area of the package that allows access to one or more products at least partially contained within the package. For purposes of the present disclosure, the term "window" refers to an area of the package that allows visibility to one or more products at least partially contained within the package. For purposes of the present disclosure, the term "port" refers to an area of the package that allows visibility and/or access to one or more products at least partially contained within the package, and as such, the term "port" can be a window and/or an opening. For clarity, packaging construction cues and visual cues, despite having different definitions, can overlap.

As used herein, the term "packaging structure" refers to the structural elements of the package that, in some embodiments, enable a packaging construction cue. For example, a packaging structural floor or wall can be provided that doesn't provide a packaging construction cue but rather provides structure to the package and/or at least partially separates at least two consumer products.

As used herein, the term "periphery" refers to a boundary, edge, change in slope of portions of the packaging structure. A periphery can assist in the indication of separate communication zones but it is understood that a communication zone can span over one or more peripheries. A periphery can be an indication of where at least one product is at least partially contained within the package.

As used herein, the term "indicium" refers to any feature that is perceivable by a person. Indicium can be visual, tactile, olfactory and/or audible. One or more indicium can overlap as a visual indicium can also have tactility, and/or an indicium producing an olfactory or audible indicium can also be visual and/or tactile. Indicium can be part of a visual cue and/or a packaging construction cue. Singular and plural forms (i.e. indicium and indicia, respectively) are used as appropriate throughout and refer to the same principle.

As used herein, the term "visual indicium" refers to a feature of the package that is visually perceivable by a person. Visual indicium can be a visual cue and/or a packaging construction cue. Visual indicium can include a graphical indicium, a symbolic indicium, a product indicium, a new or novel feature indicium, a caricature, a photograph, a picture, and/or a rendering. Visual indicium can describe quantitative and/or qualitative information. Visual indicium can be a branding indicium, a master brand indicium, and/or a sub-brand indicium.

As used herein, the term "tactile indicium" refers to a feature of the package that is perceivable to a person by touch. Tactile indicium can be a visual cue and/or a packaging construction cue. Tactile indicium can communicate quantitative and/or qualitative information. For example, tactile indicium can be in brail or provide dimensionality to an indicium such that the indicium can be understood by a person. Tactile indicium can be a branding indicium, a master brand indicium, and/or a sub-brand indicium. Tactile indicium can include a graphical indicium, a caricature indicium, and/or a symbolic indicium.

As used herein, the term "olfactory indicium" refers to a feature of the package that is perceivable to a person by smell. Olfactory indicium can be specific to a precise location on a package (i.e. "scratch-and-sniff"), can be impregnated and/or applied to a region and/or the entire package. Olfactory indicium can be applied to the product and/or the product's wrapper but can be perceivable to a person outside the package prior to opening. Olfactory indicium can be a visual cue and/or a packaging construction cue.

As used herein, the term "audible indicium" refers to a feature of the package that is perceivable to a person by sound. Audible indicium can be automated, semi-automated and thus requiring a person to interact with the product (i.e. depressing a button, tripping a sensor, etc. . . . ), and/or requiring the user to interact with the product in order to create sound. Audible indicium can be applied to the product and/or the product's wrapper but can be perceivable to a person outside the package prior to opening. Audible indicium can be a visual cue and/or a packaging construction cue.

As used herein, the term "quantitative indicium" refers to a feature of the package that describes quantity information. Quantitative indicium can comprise alphanumeric symbols or other symbols that identify and/or convey particular physical data pertaining to the contents of a package such as product count, volume, mass or weight of the package contents, absorbency, development stage, user attributes such as weight, age, height, and/or size. Quantitative indicium can be a visual cue and/or a packaging construction cue. For example, a quantitative indicium can be a packaging construction cue when the package is shaped/sized to reflect at least one quantitative indicium, the packaging structure has an aperture and/or a protrusion to describe at least one quantitative indicium, and/or is made from a material such that at least one quantitative indicium is readily apparent.

As used herein, the term "qualitative indicium" refers to a feature of the package that describes information about the product. Qualitative indicium can comprise alphanumeric symbols or other symbols that identify and/or convey particular features and/or benefits of the product(s) disposed within a respective package such as product claims. Qualitative indicium can be an indicium such as graphical indicium, a caricature indicium, a symbolic indicium, a product indicium, and/or a new or novel feature indicium.

As used herein, the term "regulatory indicium" refers to a feature of the package that describes information either required by law, regulation (i.e. set by local, state, provincial, federal, national, multi-national, global, and/or other jurisdiction) and/or is optional but responsibly included on the packaging in view of the nature of the product and/or social norms. Regulatory indicium can be quantitative indicium and/or qualitative indicium. Regulatory indicium can be a visual cue and/or a packaging construction cue. Regulatory indicium can be a product offering indicium, a warning, a correct usage, absorbency, size, and/or a scannable code indicium (i.e. UPC, QR, a unique device identifier (UDI), shipping/production/warehousing code, etc. . . . ).

Figure 2:
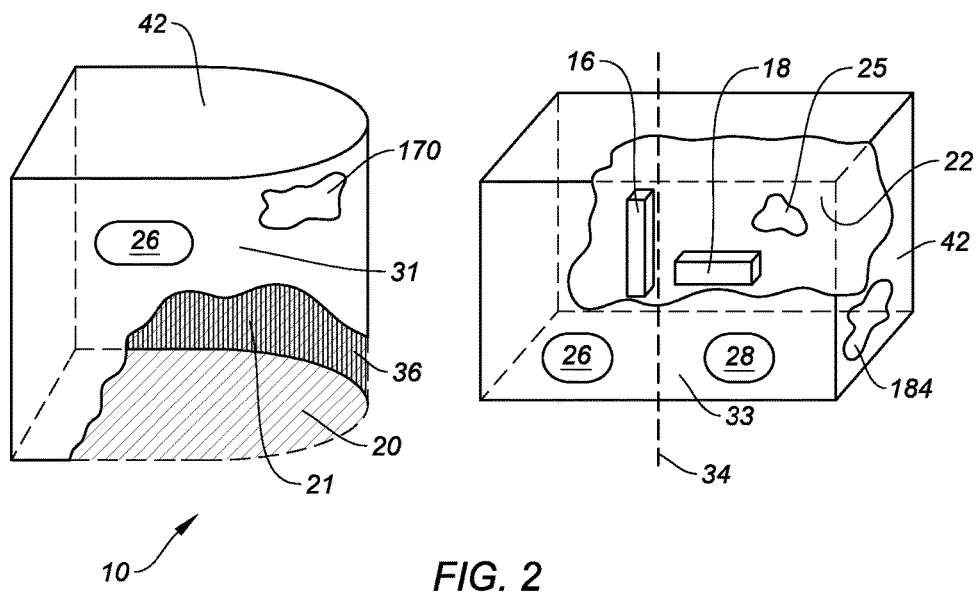
FIG. 2 is a representation of an embodiment of a packaging scheme

As generally demonstrated in the exemplary embodiments of FIGS. 1-2, the present disclosure relates to a packaging scheme 10 for at least two packages having at least two different consumer products. A first package 12 and a second package 14 each have an exterior surface 20 and an interior surface 22 defining a volume 24 that at least partially encloses a first consumer product 16. The exterior surface 20 and/or interior surface 22 can be continuous, integral, non-integral, can be one or more surfaces, and as such can yield a variety of geometries so long as the first package 12 at least partially contains the first consumer product 16 and the second package 14 at least partially contains at least the first consumer product 16 and at least a second consumer product 18. The terms "substantially contains" and "at least partially contains" describes the ability of more than one unit of a consumer product to be held together for transport and/or sale. The term "substantially contains", as used herein, refers to a product being nearly entirely contained and/or entirely contained within a package.

The first package 12 has a first indicium 26 associated with a first consumer product 16. The second package 18 also has at least the first indicium 26 and also at least a second indicium 28 associated with the second consumer product 18. In some embodiments, the first indicium 26 is on a first principal communication zone 30 on the first package 12 and is also on the second principal communication zone 32 on the second package 14. In some embodiments, the second indicium 28 is on the second principal communication zone 32 on the second package 14.

The second principal communication zone 32 can have symmetry amongst the first indicium 26 and the second indicium 28 such that a type of information can be found in the same, equal and/or opposite location about the axis of symmetry 34. The axis of symmetry 34 can be vertical, horizontal, angular, skew, or combinations thereof. Said another way, the first indicium 26 and second indicium 28 can be in a special relationship such that they are (despite not being congruent or conveying the same information) are mirror, reflected, reciprocal and/or similarly located images about an axis of symmetry 34.

In other embodiments, the second principal communication zone 32 can be divided between at least the first consumer product 16 and the second consumer product 18 such that further information can be provided about the contents of at least the first consumer product 16 and the second consumer product 18. For instance, the second principal communication zone 32 can be divided between at least the first consumer product 16 and the second consumer product 18 based on the total count of either (x) the first consumer product 16 and second consumer product 18 within the second package 14, or (y) all products within the second package 14. In other embodiments, the second principal communication zone 32 can be divided amongst at least the first consumer product 16 and the second consumer product 18 based on the volume (or likewise mass or weight or density) occupied by either (x) the first consumer product and second consumer product within the second package, or (y) all products within the second package. The volume 24 of the package may be similar to but not equal to the volume the products actually occupy. In yet other embodiments, the second principal communication zone 32 can be divided to reflect qualitative information about the products within the second package 14, such as but not limited to: absorbency, flexibility and other properties related to bending, flexing, moldability, ductility, conformability, and malleability, strength, voltage, wattage, power, lumens, hours of light, number of blades, shaves, and cleaning power.

In other embodiments, there are at least two principal communication zones on each package 30, 31 and 32, 33, respectively. The at least two principal communication zones provide similar information and in some embodiments, via similar indicium. The at least two principal communication zones mitigate situations where a package can be misoriented on the shelf such that a principal communication zone 30 or 32 can no longer be seen. FIG. 2, in an exemplary embodiment where at least two principal communication zones can be placed on different surfaces of the package such as opposite exterior surfaces of the package. In one embodiment, a first principal communication zone 30 and a second principal communication zone 31 are perpendicular to each other with respect to an axis 35. In this embodiment, a benefit is provided for packages that have differently sized communication zones and/or a package that has two dimensions that are not equal (i.e. a rectangular shape, an ovular shape, etc. . . . ) such that they can be oriented in one of two ways on a shelf depending on the available space and dimensions of the shelf. The term "shelf" as used herein, describes either a brick-and-mortar retail shelf and/or electronically displayed set of images.

As further shown in an exemplary embodiment of FIG. 2, an exterior surface 20 is translucent or has a port 36 such that a portion of the interior 21 of the package (and/or an interior surface 22) can be visible, a principal communication zone can be inside the package and/or on an interior surface 22. One of skill in the art understands that although the aforementioned are in regards to principal communication zones, the aforementioned teachings can be applied to communication zones 42 in general.

In some embodiments, a first package 12 has at least one port 36 and/or at least one portion of an exterior surface 20 that is at least partially translucent such that a portion of at least one first consumer product 16 contained within the first package 12 is visible before the at least one first consumer product 16 has been removed from the first package 12. In further embodiments a second package 14 has at least one port 36 and/or at least one portion of an exterior surface 36 that is at least partially translucent such that at least portion of at least one first consumer product 16 is visible before the at least one first consumer product 16 has been removed from the first package 12. In yet further embodiments, the at least one port 36 and/or at least one portion of an exterior surface 36 of the second package is positioned such that at least a portion of at least one first consumer product 16 and at least a portion of at least one second consumer product 18 are both visible before they are removed from the second package 14. In yet further embodiments, the second package has at least two ports 36 and/or the exterior surface 20 has at least two portions that are at least partially translucent such that a portion of at least one first consumer product 16 is visible before it is removed and a portion of at least one second consumer product 18 is also visible before it is removed, where each is visible through a separate port 36 and/or at least partially translucent portion of the exterior surface 20. In such embodiments with two ports 36, the ports can be located such that there is symmetry between the two ports 36 about an axis of symmetry 34. One skilled in the art this can be applied to a third, fourth, fifth and nth package and/or consumer product.

In some embodiments and as demonstrated in the exemplary embodiment of FIG. 2, the interior surface 22 can provide further indicium 25 that provide further information for the consumer that may not be (i) required on the exterior surface 20, (ii) may not be as significant to the consumer in communicating key information on which to make a purchasing and/or use decision as other information on the exterior surface 20, (iii) may be too detailed to be put on the exterior surface 20, (iv) may provide redundant information to the exterior surface 20 for reinforcement of certain information, and/or (v) can provide a deviation in information that seeks to improve and/or change the mental state of a consumer. Indicium 25 may include but is not limited to: product regulatory indicium 184, product coupon indicium 170, wellness information, and/or further indicium that assist the consumer in achieving an improved state of mind and/or well-being.

In further embodiments, the exterior surface 20 of the package can have a discreet appearance, while the interior surface 22 of the package can have an aspirational, celebratory, exciting and/or more creative appearance. One skilled in the art understands the interior surface 22 can have a complimentary appearance to the exterior surface 20 and/or have a unique appearance such that a different set of emotions are elicited from the consumer upon accessing and/or removing at least one consumer product from the package.

In yet other embodiments, a second package 14 has both first indicium 26 and second indicium 28 on the entire exterior surface 20 of the second package 14. In other words, the first indicium 26 and second indicium 28 appear on both the second principal communication zone 32 and all other communication zones 42 of the second package 14. In these embodiments, despite misorientation such that the second principal communication zone 32 is not fully visible to the consumer, there is visibility of the first indicium 26 and second indicium 28 such that the consumer understands that the first consumer product 16 and second consumer product 18 are both within the second package 14. One skilled in the art understands that portions of the interior 21 of the second package 14 that can be visible due to translucency and/or a port 36 within the package can also have the first indicium 26 and second indicium 28. One skilled in the art further understands that any interior surface 22 and/or the entire interior surface 22 of any package can have at least one indicium 25.

In yet further embodiments a second principal communication zone 32 is continuous over the entire exterior surface 20 of the second package 14 such that the first indicium 26 and the second indicium 28 are continuously seen from a multitude of orientations of the second package 14.

In some embodiments of the present disclosure, the two consumer products are related consumer products. In one embodiment, a first consumer product 16 is a power or energy source such as a battery and a second consumer product 18 is a lighting device. In another embodiment, a first consumer product 16 is a personal cleansing cloth (i.e. a hand, face, or body wipe) and a second consumer product 18 is an incontinence product (i.e. a diaper, incontinence pad, or other incontinence garment such as a napkin, pad, or liner). In yet another embodiment, a first consumer product 16 is a tampon and a second consumer product 18 is a menstrual and/or an incontinence product worn either internally or externally to the body (i.e. a pad, liner, an internally worn incontinence device, an incontinence garment, etc. . . . ). In yet a further embodiment, a first consumer product 16 is a razor and a second consumer product 18 is a shaving aid (i.e. pre or post shaving aids such as shaving cream, after-shave, and/or other emollients, depilatories, lubricants, anti-coagulants, etc. . . . ). In yet further embodiments, a firs consumer product 16 is a bottle and a second consumer product 18 is another mealtime product (i.e. nipples, cups, lidded cups, straws, valves, lids, bowls, plates, utensils, snack containers, lidded containers, replacement parts, cleaning tools, etc. . . . ). In yet another embodiment, a first consumer product 16 is a sunscreen and a second product 18 is another skin product (i.e. a personal cleansing cloth, a tanning product, lotion, etc. . . . ). In yet a further embodiment, a first consumer product 16 is a diaper disposal product and a second consumer product 18 is a personal cleansing cloth. In yet a further embodiment, a first consumer product 16 is a personal cleansing cloth and the second consumer product 18 is a pair of gloves. In still a further embodiment, a first consumer product 16 is a pet waste disposal device to store pet waste material and a second consumer product 18 is a pet waste disposal and/or cleansing accessory such as a plurality of surface wipes for disinfecting the pet waste area and/or pet waste disposal device; in other embodiments the second consumer product 18 is a pet waste disposal product designed for a first type of pet (i.e. a cat). One skilled in the art understands there are further permutations of related consumer goods as described throughout the present disclosure.

Figure 3:
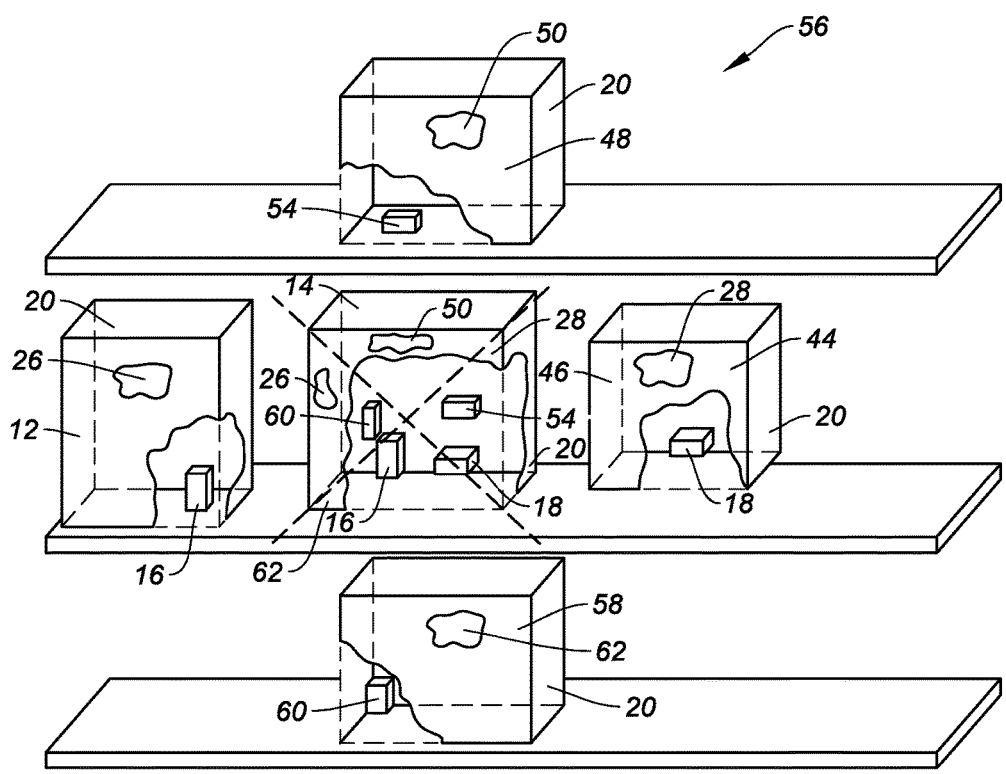
FIG. 3 is a representation of an embodiment of a shelf set array

FIG. 3 shows an exemplary embodiment of a third package 44 at least partially contains the second consumer product 18. The third package 44 has the second indicium 28 on at least the exterior surface 20. The third package 44 can have a third principal communication zone 46, and all the characteristics described throughout the present disclosure with regard to the first package 12 and second package 14.

FIG. 3 shows an exemplary embodiment of a fourth package 48. The fourth package 48 provides a third consumer product 54. The fourth package 48 has a third indicium 50 on at least the exterior surface 20. The fourth package 48 can have a fourth principal communication zone 52, and all the characteristics as described throughout the present disclosure with regard to the first package 12, second package 14, and third package 44. In some embodiments, the second package 14 at least partially contains the first product 16, the second product 18, and the third product 54. The second package 14 can also have the third indicium 50. The third indicium 50 can be located on the second principal communication zone 32. One skilled in the art understands that there can be, within reason and subject to the constraints of the types of products and types of packages, transport/distribution, retail, consumer buying preferences, etc. . . . , an nth number of consumer products that can share a common package with the aforementioned features and teachings. One skilled in the art also understands that should a single package have three, four or more different related consumer products, the principal communication zone 30 and/or other communication zone(s) 42 may be divided amongst all the different types of products such that an indicium 25 associated with each type of product is touted.

In further embodiments a shelf set array 56 is provided to assist the consumer in finding related consumer products. In one embodiment, a first package 12 at least partially containing a first consumer product 16 is adjacent (i.e. above, below, to the left, to the right, or combinations thereof) a second package 14 at least partially containing a first consumer product 16 and a second consumer product 18. In further embodiments, a third package 44 is also adjacent the second package 14, where the third package 44 at least partially contains a second consumer product 18. In yet further embodiments, a fourth package 48 at least partially containing a third consumer product 54 is also adjacent the second package 14. In some embodiments, the second package 14 at least partially contains the first consumer product 16, the second consumer product 18, and the third consumer product 54. In other embodiments, a fifth package 58 at least partially contains a fourth consumer product 60 is also adjacent the second package 14. In some embodiments, the second package 14 at least partially contains the first consumer product 16, the second consumer product 18, the third consumer product 54, and/or the fourth consumer product 60.

In embodiments where a first package 12 and a second package 14 are adjacent each other, the first indicium 26 on the second package 14 is adjacent the first package 12. In embodiments where a first package 12 and a third package 44 are both adjacent the second package 14, the first indicium 26 on the second package 14 is adjacent the first package 12 and the second indicium 28 on the second package 14 is adjacent the third package 44. In embodiments having a first package 12, a third package 44, and a fourth package 48 that are all adjacent the second package 14, the first indicium 26 on the second package 14 is adjacent the first package 12, the second indicium 28 on the second package 14 is adjacent the third package 44, and the third indicium 50 on the second package 14 is adjacent the fourth package 48. In yet another embodiment a fifth package 58 at least partially containing a fourth consumer product 60 has a fourth indicium 62. In yet further embodiments, the first package 12, third package 44, fourth package 48 and the fifth package 58 are all adjacent the second package 14 such that the first indicium 26 on the second package 14 is adjacent the first package 12, the second indicium 28 on the second package 14 is adjacent the third package 44, the third indicium 50 on the second package 14 is adjacent the fourth package 48, and the fourth indicium 62 on the second package 14 is adjacent the fifth package 58.

Figure 4:
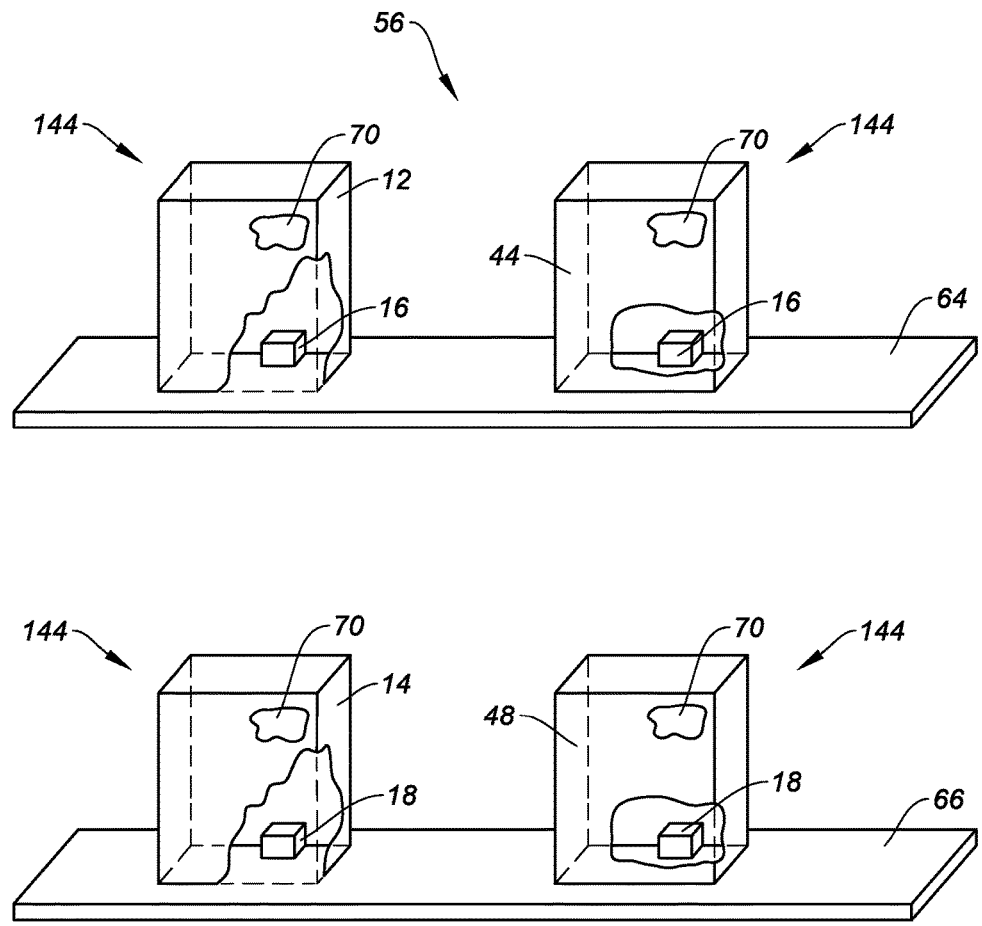
FIG. 4 is a representation of an embodiment of a shelf set array

Referring to the exemplary embodiment shown in FIG. 4, a shelf set array 56 can comprise multiple related product schemes 144 and/or packaging schemes 10 such that multiple related sets of products can be easily found based on further product characteristics. In one exemplary embodiment, a first package 12 at least partially contains a first consumer product 16 and a second package 14 at least partially contains a first consumer product 16 and a second consumer product 18. The first consumer product 16 and second consumer product 18 have the same characteristic, such as a fragrance. A third package 44 at least partially contains the first consumer product 16 and a fourth package 48 at least partially contains a first consumer product 16 and a second consumer product 18. The first consumer product 16 and second consumer product 18 at least partially contained in the third package 44 and fourth package 48, respectively, are perceived to have no fragrance. In one shelf set array 56, the first package 12 and second package 14 are on a first shelf 64 while the third package 44 and fourth package 48 are on a second shelf 66 adjacent to the first shelf 64. The adjacency of the first shelf 64 and second shelf 66 provides proximity amongst the four packages such that the consumer can quickly understand the offerings amongst the four packages. In a further embodiment, the four packages share at least one first indicium 30 such that it is clear that all four packages carry related consumer goods. In a further embodiment, the four packages have at least one indicium 70 that is different such that it is clear that all four packages provide a different consumer product and/or a consumer product with a different feature. One skilled in the art understands that instead of fragrance, a different attribute of the product such as but not limited to: color and/or aesthetics, absorbency, power, sharpness, volume, size, age, and time/length of/for usage, can be a distinguishing attribute. One skilled in the art further understands that a fifth, sixth, or nth package, a third, fourth or nth related consumer product, and/or a third, fourth or nth shelf are within the scope of the present disclosure.

Figure 5:
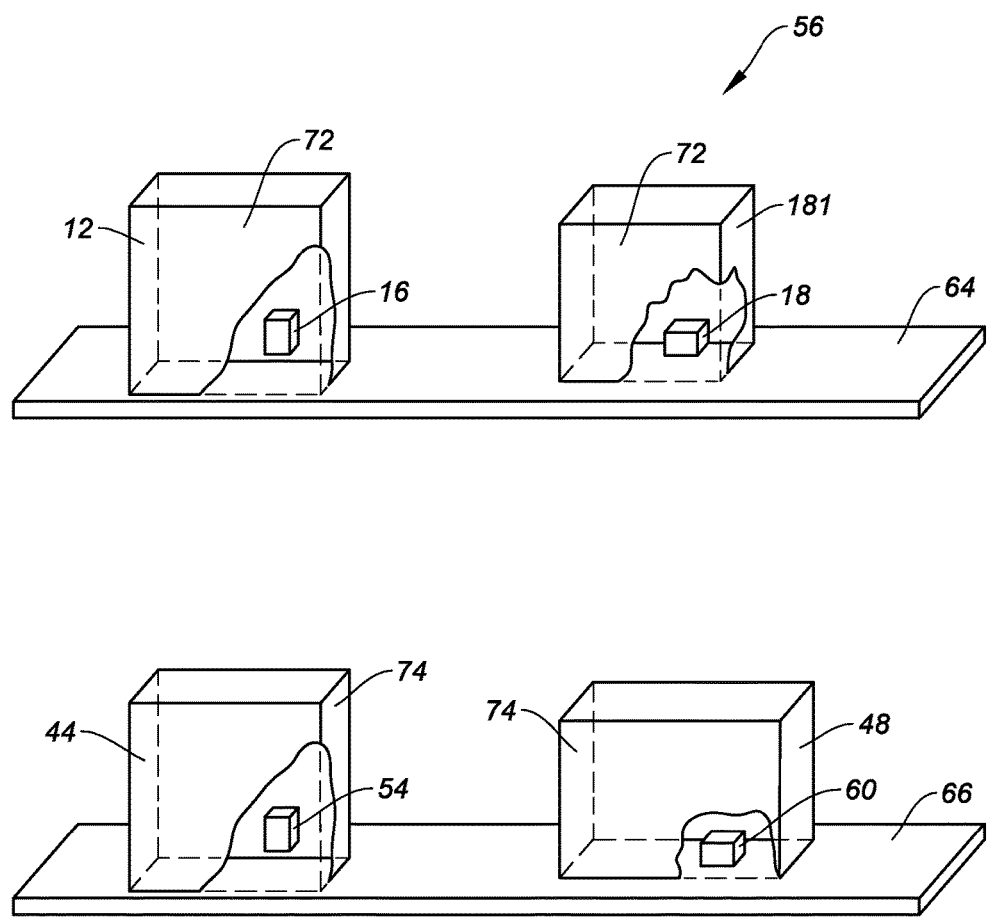
FIG. 5 is a representation of an embodiment of a shelf set array

Referring to the exemplary embodiment shown in FIG. 5, different tiers of products, based on relative product quality, performance, materials, and/or price, are provided. A shelf set array 56 having a first product tier 72 is located on a first shelf 64, while a second product tier 74 is located on an adjacent second shelf 66. In another embodiment, a first product tier 72 are located in a vertical orientation spanning at least a first shelf 64 and a second shelf 66, while a second product tier 74 is located adjacent the first product tier 64 on at least the first shelf 64 and the second shelf 66. In a further embodiment, a first consumer product 16 within the first product tier 72 correlates to a second product 18 in a second product tier 74. In one embodiment, the first product 16 is adjacent the second product 18 on a first shelf 64. In another embodiment, the first product 16 is on a first shelf 64 and is adjacent (i.e., directly below or above) the second product 18 on the second shelf 66. One skilled in the art further understands that an nth product tier, an nth shelf, an nth product in the first product tier 72, and/or an nth product in the second product tier 74 are within the scope of the present disclosure.

Figure 6:
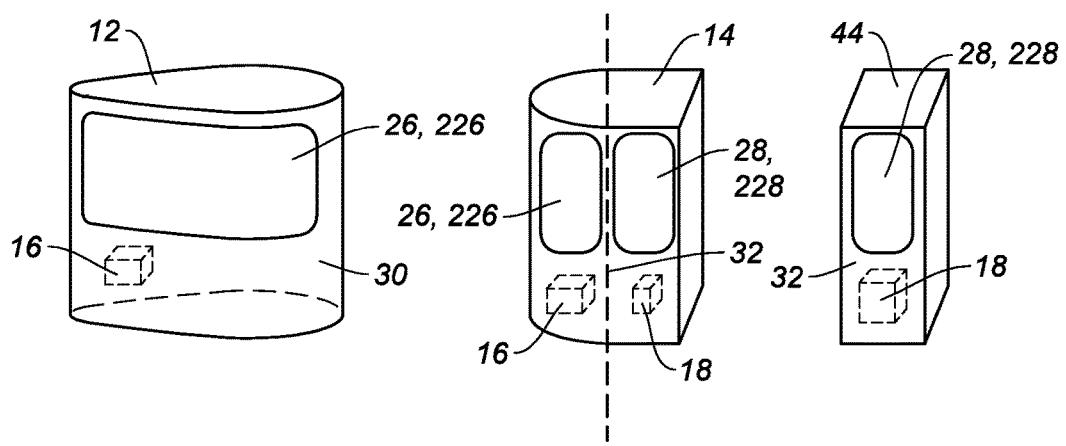
FIG. 6 is a representation of an embodiment of a packaging scheme

Referring to FIG. 6, the first indicium 26 and the second indicium 28 can be visual cues and/or package construction cues. In one embodiment, the first indicium 26 and the second indicium 28 are both visual cues. In another embodiment, the first indicium 26 and the second indicium 28 are both package construction cues. It can be preferable to have the indicium 25 for each consumer product be the same type of indicium 25 such that it is simpler for the consumer to spot the related products. For instance, in one embodiment the first indicium 26 is a visual indicium having a first predominant color 226, while the second indicium 28 is a visual indicium having a second predominant color 228. In another exemplary embodiment where the indicium 25 are packaging construction cues, the first indicium 26 is an arcuate panel forming at least a partially cylindrical structure while the second indicium 28 are a series of three panels that meet to form two edges thereby forming part of a prismatic rhomboid, trapezoid, rectangle and/or square. The first package 12 has the first indicium 26 and thus has at least a partially arcuate shape, while a second package 14 also has the first indicium 26 that is at least a partially arcuate shape that connects to the second indicium 28 having at least three panels forming two edges. A third package 44 can also provide the second indicium 28 and thus form a third package 44 having at least three panels that meet to form at least two edges. As such, the consumer would readily understand that the indicium in the form of a packaging construction cue correlates to the consumer product at least partially contained within the package. In some embodiments, the packaging construction cue provides a qualitative cue associated with the product such as but not limited to: product shape, mechanical properties of the product, and product material(s). One skilled in the art understands visual cues and packaging construction cues are not so limited to the aforementioned examples but can be as described or understood throughout the specification.

In some embodiments, a visual cue appears to be a packaging construction cue. In this embodiment, the visual cue has visual and/or tactile indicium that create(s) an illusion of the package having a structure different than it has in actuality. The visual cue could be a pattern such as stripes, arcuate lines and/or shapes, dots, a dot matrix, and/or a hologram. In some embodiments, the visual cue is applied to the product and/or the wrapper of the product such that a similar illusory appearance is perceived by a consumer.

As used herein, the term "color" describes an individual's perception of the spectral composition of visible light coming from a portion of an object. Color characteristics include hue, saturation and luminosity. Each is a separate color characteristic. Hue is the attribute of a color that allows it to be classified as a given color. Saturation, which is sometimes referred to as vividness, is the intensity of the color. Saturation is the degree of freedom from gray. Luminosity, sometimes referred to as value, is the degree of lightness (paleness) or darkness in a color. For example, a blue with white added is a pale color, e.g. baby blue, and blue with black added is a dark color, e.g. navy blue. Color and the related characteristics of color can be determined by the Hunter Color Test as described below.

Figure 8:
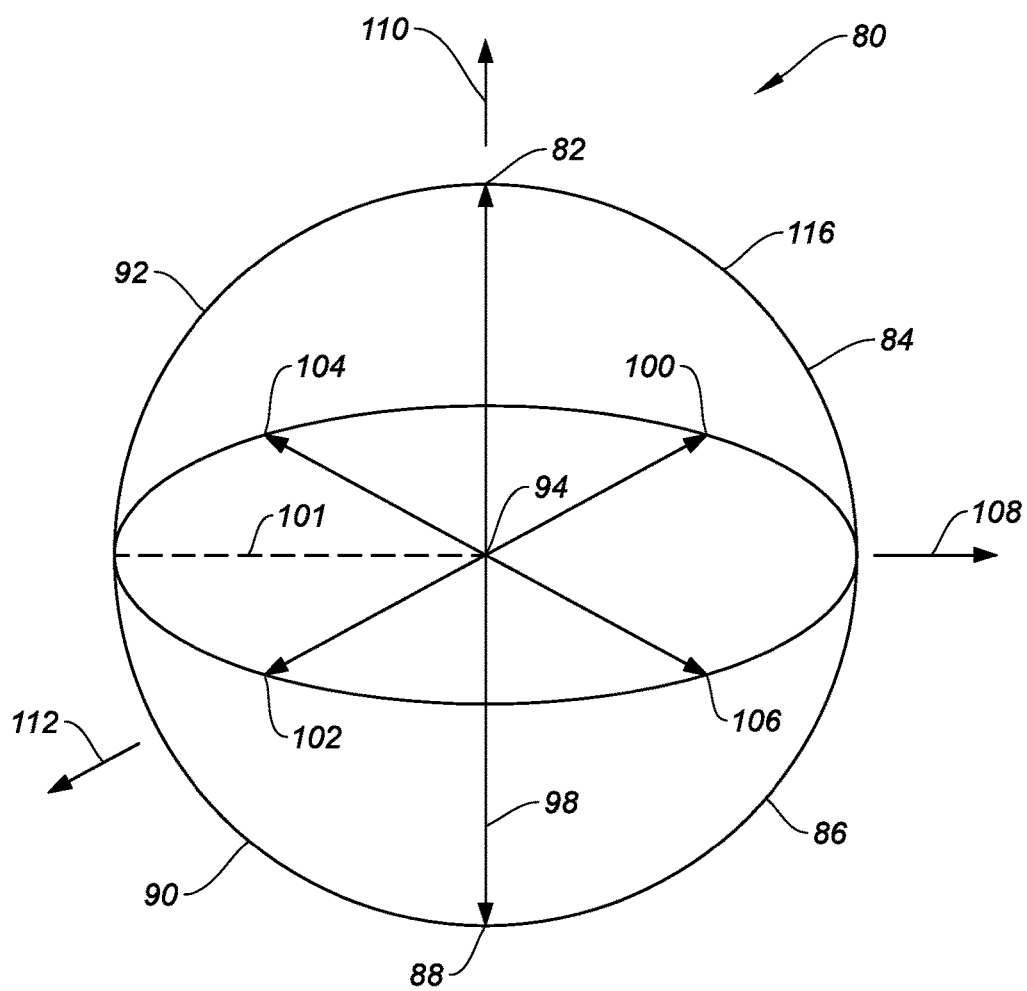
FIG. 8 is a representation of an embodiment of a diagram used to characterize color

Color 80 can have a particular hue, luminosity and saturation/vividness can be applied to an internationally recognized 3-dimensional solid color chart as would be well-known to those skilled in the art, such as the color chart of FIG. 8, and can be utilized to determine whether a color is the "same", "different" or a "shade". For example, the hue of a particular color can be applied to the color chart along circle 116 having 360 degrees. The colors 80 white 82, red 84, blue 86, black 88, green 90, yellow 92, and gray 94 are shown in general regions about circle 116. Luminosity is shown to vary from a first end 96 to a second end 98. Saturation is the degree of freedom from gray 94. Hue varies between 100, 102, 104, and 106 to establish the color 80 as described about circle 116. Thus, two colors are considered to be the same herein when they have first and second respective hues that are 30° apart from each other or less, such as 20° apart from each other or less, or 10° apart from each other or less, when viewed along circle 116. In addition, the value (luminosity) of a color 80 can be applied to the color chart demonstrated in FIG. 8, along the z-axis 110 between white and black. For clarity, the x-axis 108 and y-axis are also defined. Luminosity is measured on a scale from white to black. By way of example only, a luminosity of 100% equates to white, while a luminosity of 0% equates to black. Thus, in some aspects, two colors are considered to be the same herein when they also have a luminosity difference of 30% or less, such as 20% or less, or 10% or less of the maximum of the z-axis 108 (using the Polaroid white reference standard). Further, the saturation/vividness (chroma) of a color 80 can be applied to the color chart along the length of the radius 101. Thus, in some aspects, colors are also considered to be the same herein when the have a saturation/vividness difference of 40% or less, such as 25% or less, or 10% or less of colors outside the ranges for colors that the "same" are considered "different". In addition, two colors that are the same but have different values for at least one of the hue, luminosity, and/or saturation/vividness within the ranges for a color 80 being the same is considered to be a "shade". Thus, as applied herein, given two colors, where one color 80 is a shade of the other color 80, they are considered to be the same color 80.

Figure 7:
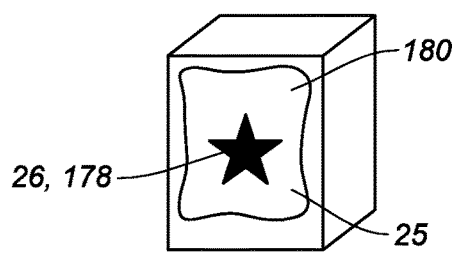
FIG. 7 is a representation of an embodiment of an indicium

Referring to the embodiments shown in FIGS. 6 and 7, a first indicium 26 associated with a first consumer product 16 is a first color 226. A second indicium 28 associated with a second consumer product 18 is a second color 228. The first consumer product 16 and the second consumer product 18 are related consumer products. The first indicium first color 226 and the second indicium second color 228 are different. A first consumer package 12 at least partially contains a first consumer product 16. The first consumer package 12 has a first principal communication zone 30 that has a color that is substantially entirely the first indicium first color 226. The term "substantially entirely" as used herein describes a characteristic that is a dominant and/or majority of a given attribute or indicia. A second consumer package 14 at least partially contains at least a first consumer product 16 and a second consumer product 18. The second consumer package 14 has a second principal communication zone 32 that has a first indicium 26 and a second indicium 28. The portion of the second principal communication zone 32 having the first indicium 26 is substantially entirely the first indicium first color 226. The portion of the second principal communication zone 32 having the second indicium 28 is substantially entirely the second indicium color 228. In further embodiments, a third package 44 at least partially contains the second consumer product 18. The third package 44 has a third principal communication zone 52 having a second indicium 28. The third principal communication zone 46 has a color that is substantially entirely the second indicium color 228. The first indicium color 226 and second indicium color 228 are different. As demonstrated in FIG. 7, indicium 25 may overlap the first indicium 26 and/or second indicium 28, and as such, the first indicium color 226 and/or second indicium color 228 may appear to be in the forefront 178 and/or a background 180 color when considered in the totality of the first package 12, second package 14, third package 44, nth package. One skilled in the art understands that other embodiments can include without limitation: a pattern, texture, and/or translucency, in addition to and/or in lieu of color.

Figure 9:
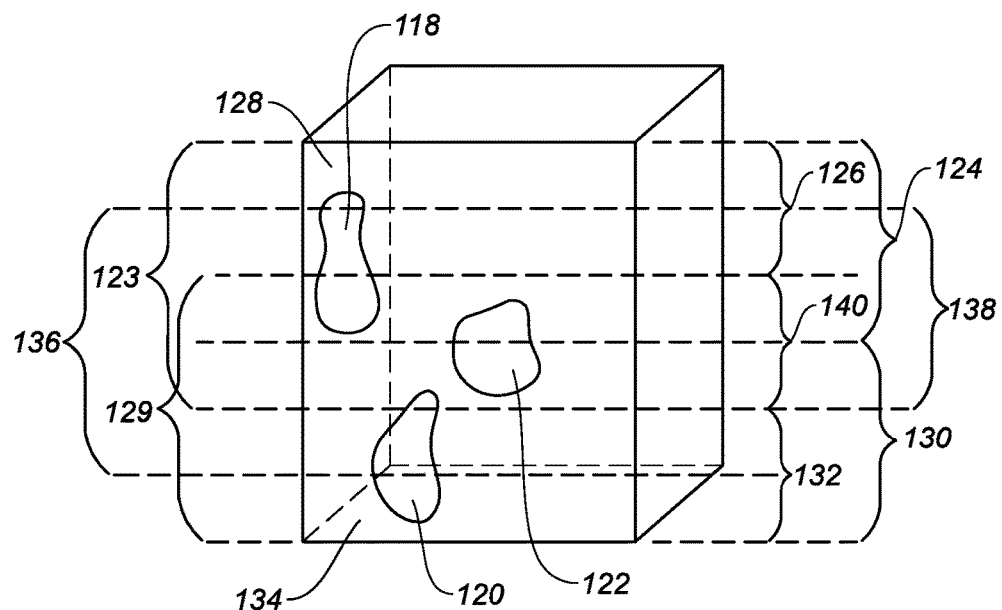
FIG. 9 is a representation of an embodiment of an indicium
Figure 10:
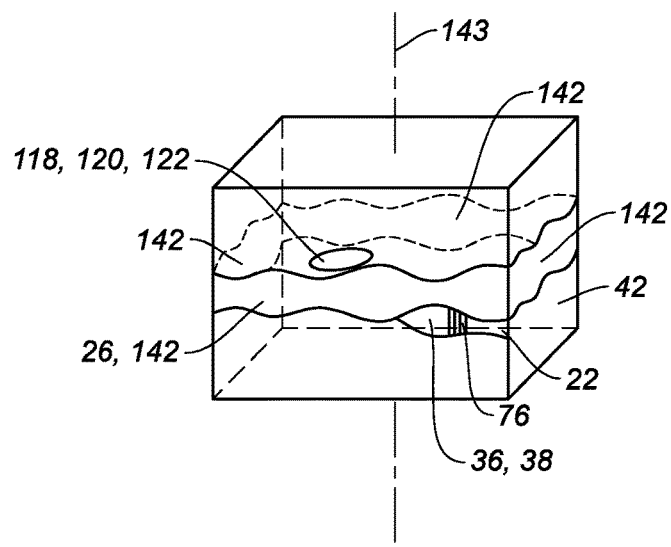
FIG. 10 is a representation of an embodiment of an indicium

As shown in FIGS. 9 and 10 master brand indicium 118 can provide context and/or continuity amongst several related consumer products. In some embodiments where related consumer products have different brands, the master brand indicium 118 can provide further continuity as to who the manufacturer or the seller of the product is. A master brand indicium 118 can be presented on a first package 12 and/or a second package 14. The second package 14 can have a master brand indicium 118 on the second principal communication zone 32 such that it is at least partially in both (i) a first indicium 26 associated with a first consumer product 16 at least partially contained in the second package 14 and (ii) a second indicium 28 associated with a second consumer product 18 at least partially contained in the second package 14.

In some embodiments, a master brand indicium 118 is located at the top portion 123 of the package, or preferably the top half 124 of the package, or more preferably, the top third 126 of the package, or most preferably, in the top-most portion 128 of the package (i.e. closest to the top-end of the principal communication zone). In some embodiments, a master brand indicium 118 is located on the bottom-most portion 134 of the package, or preferably the bottom half 130, or more preferably, the bottom third 132 of the package, or most preferably, the bottom-most portion 134 of the package ((i.e. closest to the bottom-end of the principal communication zone). In other embodiments, the master brand indicium 118 is located on the principal communication zone. In these embodiments, it is preferable that the master brand indicium 118 be sized and placed such that it is easy to identify. In these embodiments, the master brand indicium 118 provides reassurance to the consumer that the related consumer products have particular attributes that the consumer identifies with the master brand indicium 118. In other embodiments, the master brand indicium 118 can be on a communication zone 42. In these embodiments, the master brand indicium 118 can be on the bottom portion 129 of the package, or preferably the bottom half 130 of the package, or more preferably, the bottom third 132 of the package, or most preferably, on the bottom-most portion 134 of the package. In these embodiments, the master brand indicium 118 does not add significant value and/or reassurance to the consumer and as such, the master brand indicium 118 can be de-emphasized in placement, aesthetic and/or size on the package.

A brand indicium 120 is provided on the package. Preferably, the brand indicium 120 is at least provided in the principal communication zone, but it can also be provided on other communication zones. The brand indicium 120 can be utilized for one or more consumer products such as a first consumer product 16 and a second consumer product 18. In one embodiment, a second package 14 at least partially contains at least a first consumer 16 product and a second consumer product 18. The second package 14 has a second principal communication zone 32 having at least a first indicium 26 and a second indicium 28. The brand indicium 120 at least partially spans both (i) the first indicium associated with a first consumer product at least partially contained in the second package and (ii) a second indicium 28 associated with a second consumer product 18 at least partially contained in the second package 14. The brand indicium 120 is sized and placed such that it is easy to identify. In some embodiments, the brand indicium 120 is placed in the top portion 123 of the package, or preferably the top half 124, or more preferably the top third 126 of the package. In other embodiments, the brand indicium is in the middle portion 136 of the package, or preferable the middle half 138 of the package, or more preferably the middle third 140 of the package.

A sub-brand indicium 122 is provided on the package. In one embodiment, the sub-brand indicium 122 is adjacent the brand indicium 120. Preferably, the sub-brand 122 indicium is at least provided in the principal communication zone, but it can also be provided on other communication zones. The sub-brand indicium 122 can be utilized for one or more consumer products such as a first consumer product 16 and a second consumer product 18. In one embodiment, a second package at least partially contains at least a first consumer product 16 and a second consumer product 18. The second package 14 has a second principal communication zone 32 having a first indicium 26 and a second indicium 28. The sub-brand indicium 122 at least partially spans both (i) the first indicium 26 associated with a first consumer product 16 at least partially contained in the second package 14 and (ii) a second indicium 28 associated with a second consumer product 18 at least partially contained in the second package 14. The sub-brand indicium 122 is sized and placed such that it is easy to identify. In some embodiments, the sub-brand indicium 122 is in the top portion 123 of the package. In other embodiments, the sub-brand indicium is in the middle portion 136 of the package, or preferably the middle half of the package 138, or more preferably the middle third 140 of the package. In yet other embodiments, the sub-brand indicium is in the bottom half 130 of the package. One skilled in the art understands the sub-brand indicium 122 may be placed anywhere on the package so long as it is readily apparent to the consumer and to the product(s) to which it is associated with.

In yet a further embodiment, a packaging scheme is provided wherein at least one of the visual, audible, olfactory and/or tactile indicium is provided on at least one communication zone 42 of the package that is not the principal communication zone a consumer can initially identify. In one embodiment, the at least one indicium 26 is provided on both the principal communication zone and another communication zone 42. In one embodiment, the at least one indicium 26 is continuous about the entire package. In yet a further embodiment, the at least one indicium 26 is a swoosh 142. The term "swoosh" as used herein, refers to a convex, curvilinear, planar shape, stripe, wave, swoosh and/or combinations thereof.

Figure 11:
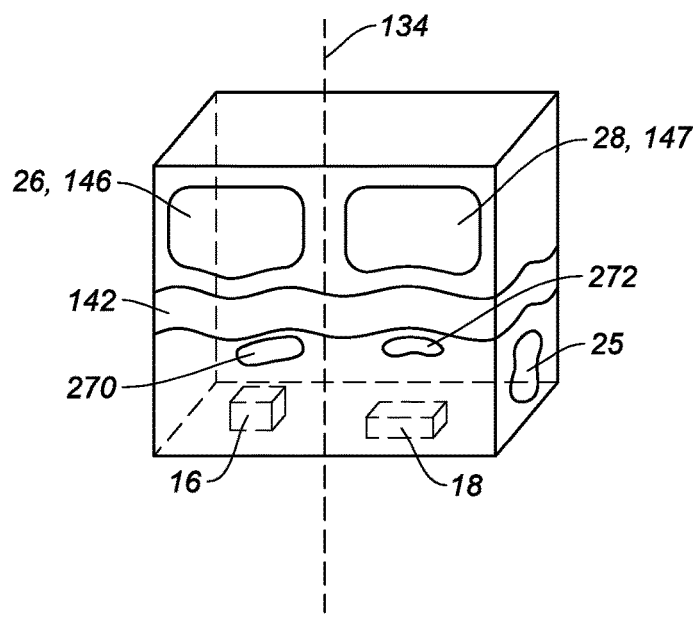
FIG. 11 is a representation of an embodiment of an indicium
Figure 12:
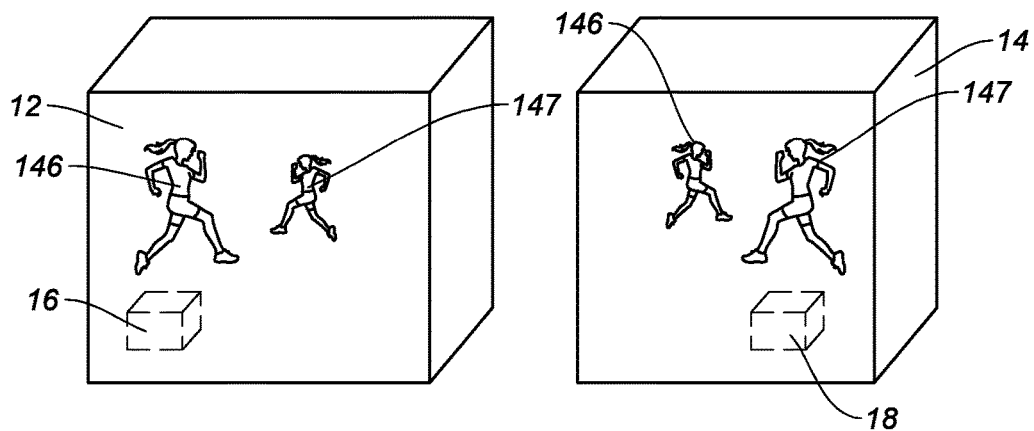
FIG. 12 is a representation of an embodiment of an indicium
Figure 13:
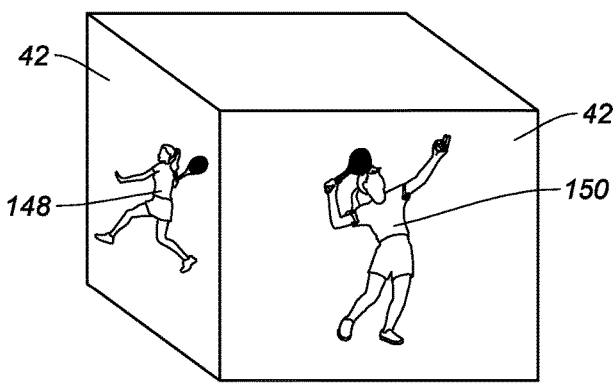
FIG. 13 is a representation of an embodiment of an indicium
Figure 14:
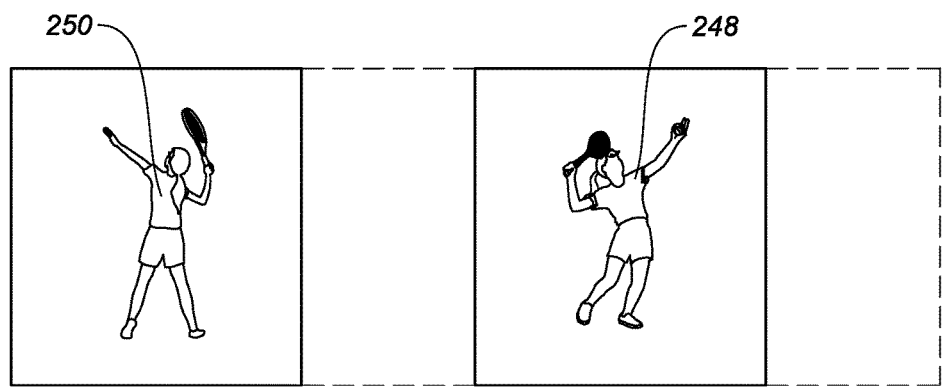
FIG. 14 is a representation of an embodiment of an indicium
Figure 15:
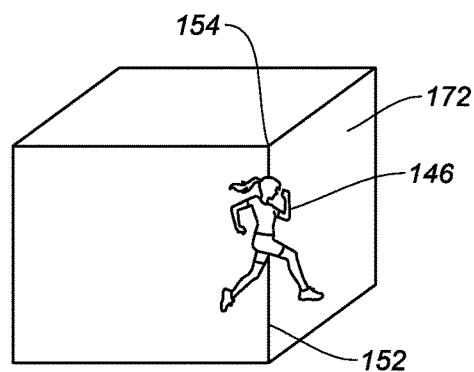
FIG. 15 is a representation of an embodiment of a indicium

As shown in the embodiments demonstrated by FIGS. 10 and 11, the swoosh 142 is continuous about the entire package such that when the package is in an initial, upright position and having a vertical axis 143, the swoosh 142 is continuous about the package such that it can be seen as the package is rotated about its vertical axis 143. In further embodiments, brand indicium 120, sub-brand indicium 122 and/or master-brand indicium 118 can be provided within and/or adjacent to the swoosh 142. In a further embodiment, other information such as absorbency, fragrance, and/or size can be provided within and/or adjacent the swoosh 142. In further embodiments, quantitative indicium 270 and/or qualitative indicium 272 are adjacent the swoosh 142 and compliment it such that any deviations in slope or changes in the aesthetics of the swoosh 142 are complimented by the adjacent quantitative indicium and/or qualitative indicium. In yet further embodiments, a port 36 such as a window 38 can further compliment the swoosh 142 such that the swoosh 142 is further accentuated by either the appearance of the product(s) and/or their wrapper(s) at least partially contained within the package and/or another interior surface 22 of the package that may provide other and/or further complimentary indicium. One skilled in the art understands that the aesthetics of the swoosh 142 and/or the information provided within and/or adjacent to the swoosh 142 can vary.

In embodiments having a package that at least partially contains a first consumer product 16 and a second consumer product 18, a swoosh 142 may be continuous across a principal communication zone that has a first indicium 26 associated with the first consumer product 16 and a second indicium 28 associated with the second consumer product 18. The swoosh 142 may have a different aesthetic, such as color, hue, translucency, pattern, texture, scent, and/or shape as it approaches, is adjacent to, touches and/or intersects the first indicium 26 and second indicium 28, such that the consumer understands that the two consumer products are related and that there is at least one difference between the two consumer products.

In some embodiments, the port 36 and/or partially translucent portion of the exterior surface can accentuate swoosh 142 such that the port 36 and/or partially translucent portion is adjacent the wave-form of the swoosh 142. In some embodiments, the swoosh 142 can be a port and/or an at least partially translucent portion of the exterior surface 20. The at least partially translucent portion of the exterior surface can be a gradient of an aspect of color (i.e. hue, luminosity, saturation/vividness, shade, etc. . . . ) and/or a spectrum of at least two different colors. In some embodiments, the spectrum of at least two different colors corresponds to a first visual indicium 26 of at least one first consumer product 16 and a second visual indicium 28 of at least one second consumer product 18. In some embodiments where the swoosh 142 extends about at least two panels, the port 36 and/or at least partially translucent portion of the exterior surface 20 that is within the swoosh 142 and/or adjacent the swoosh 142 has a gradient and/or spectrum that varies to correspond to the at least one first product 16 and/or the at least one second product 18 contained within the package that is visible through said port 36 and/or the at least partially translucent portion of the exterior surface 20.

Referring to the embodiments shown in FIGS. 11-15, various indicia 25 can be used to further describe characteristics of one or more related consumer goods within a product scheme 144, a packaging scheme 10, and/or a shelf set array 56. For instance, a graphical indicium 146 can be provided on a package. A graphical indicium 146 can be a caricature, cartoon, picture or image that is associated with the product, brand, master-brand and/or sub-brand, and/or combinations thereof. In one embodiment, a first graphical indicium 146 is associated with a first consumer product 16. In a further embodiment, a second graphical indicium 147 is associated with a second consumer product 18 that is related to but different than the first consumer product 16. The second graphical indicium 147 is also related to the first graphical indicium 146 but is likewise different in at least one aspect. For instance, in one exemplary embodiment, the first graphical indicium 146 is a caricature or cartoon of a girl or woman partaking in a first activity. The caricature can optionally be a silhouette. The activity can optionally be an athletic or social activity such as but not limited to: a team or individual sport, a party, or dancing. The second graphical indicium 147 can also be a caricature or cartoon of a girl or woman partaking in a second activity. In a further exemplary embodiment, the first graphical indicium and the second graphical indicium are partaking in different athletic or social activities. In a further exemplary embodiment, the first graphical indicium 146 and the second graphical indicium 147 have a different aesthetic. Optionally, the first graphical indicium 146 and the second graphical indicium 147 can have a different aesthetic but are the same color or are a shade of the same color. In further exemplary embodiment, the vividness of a first graphical indicium 146 with respect to a second graphical indicium 147 can indicate how or when the first consumer product 16 (associated with the first graphical indicium 146) and the second consumer product 18 (associated with the second graphical indicium 147) are to be used. For instance, if a first consumer product 16 is meant to be used primarily, first and/or during the day while a second consumer product 18 is meant to be used as a redundancy, secondly, and/or at night, the first graphical indicium 146 can be more vivid and/or less vivid than the second graphical indicium 147.

In embodiments having two graphical indicium, a first package 12 at least partially containing at least a first consumer product 16 has a first graphical indicium 146, and a second package 14 at least partially containing at least a first consumer product 16 and at least a second consumer product 18 has both a first graphical indicium 146 and a second graphical indicium 147.

In further embodiments having two graphical indicium, both the first graphical indicium 146 (associated with a first consumer product 16) and the second graphical indicium 147 (associated with a second consumer product 18) are provided on both a first package 12 at least partially containing at least the first consumer product 16 and a second package 14 at least partially containing at least the second consumer product 18. The first graphical indicium 146 on the first package 12 is more visually apparent (i.e. bolder, more vivid, in the forefront) than the second graphical indicium 147. The second graphical indicium 147 on the second package 14 is more visually apparent (i.e. bolder, move vivid, larger, in the forefront) than the first graphical indicium. In these exemplary embodiments, the packaging scheme 10 amongst the two product schemes is at least partially based in both the first graphical indicium 146 and second graphical indicium 147 being on both the first package 12 and second package 14. One skilled in the art understands that a third, fourth or nth package, consumer product, and/or graphical indicium can be provided and be within the scope of the present disclosure.

In a further embodiment an indicium can be provided in multiple communication zones 42 such that the indicium 25 has a perceivable dimensionality, such as depth. In one embodiment, an indicium 25 such as a graphical indicium 146 is provided in at least two communication zones such that a first perspective 148 and a second perspective 150 of the graphical indicium 146 are provided (i.e. a profile perspective and a front perspective, respectively). In a further embodiment, the at least two communication zones are adjacent. In a further embodiment, the at least two communication zones are opposite, such that a front perspective 248 and a rear perspective 250 of an indicium 25 can be provided. In yet a further embodiment, an indicium such as a graphical indicium 146 is in concert with a packaging construction cue such that the packaging structure 172 is flexible and enables a graphical indicium 146 to appear to be moving, have a dimensionality and/or depth. In a further embodiment, an indicium 25 such as a graphical indicium 146 is in concert with a packaging structure such as an edge 152 or a corner 154 and enables the graphical indicium 146 to soften the edge 152 and/or corner 154, and/or provide dimensionality and/or depth to the package. In other words, packaging structure 172, packaging construction cues, and other indicium 25 such as graphical indicium 146 can be used in concert amongst one or more communication zones 42 to enhance the packaging scheme 10, product scheme 144, shelf set array 56, tie together and/or separate one or more communication zones 42, and/or provide an added aesthetic, dimensionality and/or depth to the package.

Figure 16:
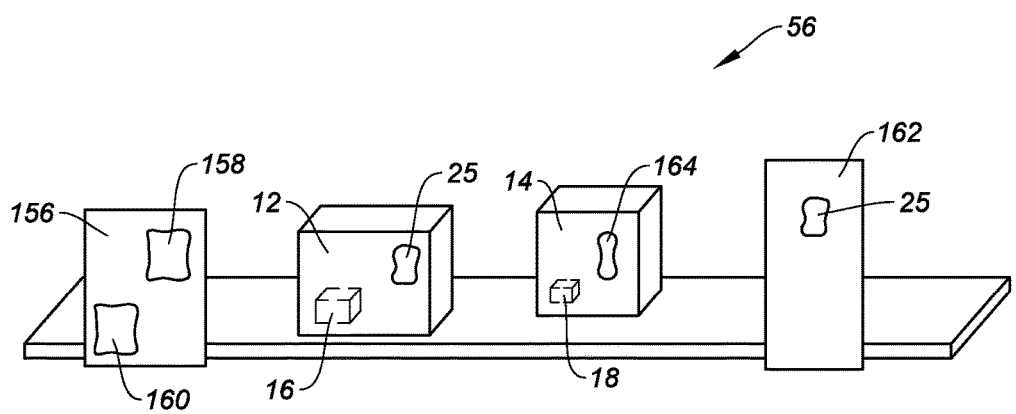
FIG. 16 is a representation of an embodiment of an packaging scheme

As shown in the embodiment of FIG. 16, a shelf set array 56 is provided with adjacent advertising material(s) 156. In these embodiments, the at least one advertising material 156 describes at least one consumer product 16 being sold in at least one package 12. The at least one advertising material 156 has a first indicium 158 that is common to the first package 12 at least partially containing a first consumer product 16. In some embodiments, the at least one advertising material 156 has one or more indicium 158 that correlate to one or more indicium 25 on the at least one package 12. In further embodiments, the one or more indicium 158 positioned on the at least one advertising material 156 and the at least one package 12 such that the indicium 25, 158 are located in at least one of a proportional and/or geographically similar manner. In some embodiments, the at least one advertising material 156 has a second indicium 160 that contrasts with at least one indicium 25 on the at least one package. In these embodiments, the second indicium 160 having contrast (i) harmonizes with and/or compliments the at least one product package 12 and optionally provides an appearance that is more impactful and/or more appealing to at least one of the sense to at least one group of consumers, (ii) drives and/or focuses the consumer back onto the at least one package 12, (iii) ties to at least one other advertisement 162 about the at least one consumer product 16, (iv) ties to at least one of a second product package 14 and/or second advertising material 162 that describes a second consumer product 14. In some embodiments, the first consumer product 16 and the second consumer product 18 are different but related consumer products. In embodiments for electronic and/or digital retail, adjacent advertising materials 156 such as banner ads and pop-up ads may be on the same page as the consumer product, and/or on a page adjacent (i.e. before or after) the page the consumer product can be viewed.

Figure 17:
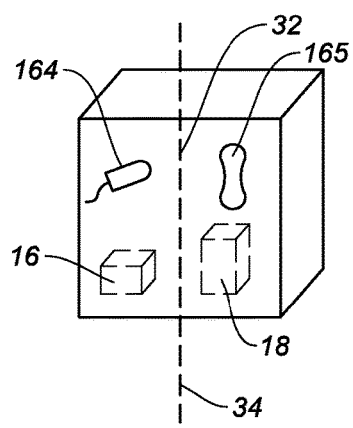
FIG. 17 is a representation of an embodiment of an indicium

Referring to the embodiment shown in FIG. 17, a product indicium 164 can be provided on a package that describes at least an attribute of the product at least partially contained within the package. For instance, a product indicium 164 can be a caricature, cartoon, picture, photo, rendering, image and/or silhouette of the product itself and/or a consumer interacting with the product. A product indicium 164 can include alpha-numeric characters as well in the form of qualitative indicium 270 and/or quantitative indicium 272. In packages at least partially containing two products, a first product indicium 164 and a second product indicium 165 may be placed on a principal communication zone 32 such that there is symmetry between the two indicium.

Figure 18:
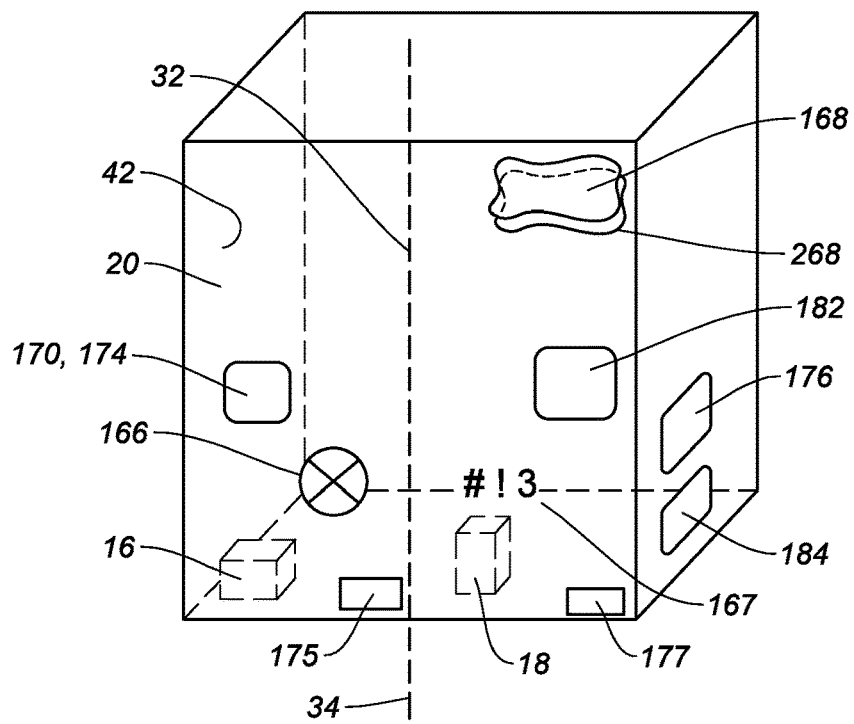
FIG. 18 is a representation of an embodiment of an indicium

Referring to the embodiment shown in FIG. 18, symbol indicium 166 can be provided on a package that describes at least an attribute of the product at least partially contained within the package. An attribute can be either something that the product possesses or something the product does not possess or does not contain. A symbol indicium 166 can include alpha-numeric characters as well in the form of qualitative and/or quantitative information. For instance, a symbol indicium 166 can be a caricature, cartoon, picture, photo, rendering, image and/or silhouette of how the product responds during use. In another embodiment, a symbol indicium 166 can be of a substance that is not included within the consumer product. In packages at least partially containing two products, a first symbol indicium 166 and a second symbol indicium 167 may be placed on a principal communication zone 32 that there is symmetry between the two symbol indicium.

A new or novel indicium 168 can be provided on a package that describes at least an attribute of the product at least partially contained within the package. An attribute can be something new or unique to the consumer product that has not been done before and/or indicate the consumer product is in its entirety completely new or different. A new or novel indicium 168 can include alpha-numeric and/or other characters as well in the form of qualitative and/or quantitative information. For instance, a new or novel indicium 168 can be a caricature, cartoon, picture, photo, rendering, image and/or silhouette of how what the new or novel attribute is, including how a person would interact with the feature and/or the product by virtue of the new feature. In another embodiment, a new or novel indicium 168 can be a caricature of a substance that is now no longer included within the consumer product. In packages at least partially containing two products, a first new or novel indicium 168 and a second new or novel indicium 169 may be placed on a principal communication zone 32 such that there is symmetry between the two indicium. In some embodiments, a new or novel indicium 168 is at the top portion 123 of the principal communication zone, preferably in the top half 124 of the principal communication zone, more preferably in the top third 126 of the principal communication zone, and most preferably, in the upper right-hand and/or upper left-hand corner of the principal communication zone (i.e. near two upper ends of the principal communication zone). The new or novel indicium 168 has aesthetics and/or is in a size, font, color that makes it prominent and/or stand-out from the rest of the package.

In some embodiments, a new or novel indicium 168 is removable (i.e. can be separated and removed from the package by a perforation, sticker, etc. . . . ). In some embodiments, upon removal of the new or novel indicium 168, a second indicium 268 is revealed. The second indicium 268 has a substantially similar size, shape and placement on the package as the new or novel indicium 168.

Figure 19:
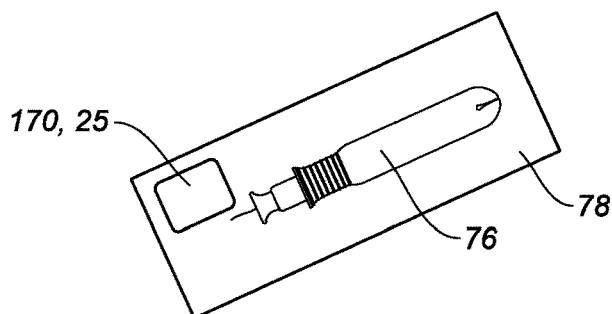
FIG. 19 is a representation of an embodiment of a product and a wrapper

Referring to the embodiment shown in FIGS. 18 and 19, a product coupon indicium 170 provides a coupon, offer for discount, and/or promotion that a consumer can partake in in hopes of garnering a prize. The product coupon indicium 170 can be for the product(s) provided within the package and/or a different product. A product coupon indicium 170 can be removable from the package. A product coupon indicium 170 can be removable from the exterior surface 20, interior surface 22 and/or a packaging structure 144 of the package (i.e. can be separated and removed from the package by a perforation, sticker, etc. . . . ) and upon removal can reveal a second indicium 268. A product coupon indicium 170 can also be located in the interior 21 the package such that it is not attached to the package itself. In further embodiments, a product coupon indicium 170 can be located on the wrapper 78, within the wrapper 78 and/or adjacent a product 76.

A product offering indicium 174 can be provided on a package that describes differences amongst one or more related consumer products. In one exemplary embodiment, a product offering indicium 174 describes various attributes of one consumer product (i.e., fragrance, size, absorbency, color, how the product interacts with the person, etc. . . . ) In a second exemplary embodiment, a product offering indicium 174 describes various attributes of at least two related consumer products that can be used in concert (i.e. in series and/or in parallel). In a further exemplary embodiment, the product offering indicium 174 describes the varieties of attributes of the at least two related consumer products that are available to a consumer for purchase. In some embodiments, the product offering indicium 174 is required by one or more local, regional, state, provincial, federal, national, global, regional and/or other jurisdictional laws or regulations.

In some embodiments, the product offering indicium 174 is on a communication zone 42 other than the principal communication zone 30. In embodiments having a package that at least partially contains two related consumer products, one or more product offering indicium 174 may be located on a communication zone directly opposite to a principal communication zone. In other embodiments, the product offering indicium 174 may be located in a communication zone 42 adjacent the principal communication zone 32.

In other embodiments, a first product offering indicium 174 describing a first consumer product 16, and a second product offering indicium 176 describing a second consumer product 18, are located on separate communication zones 42, 43 that are each adjacent a principal communication zone 32. The first product offering indicium 174 is located on a communication zone 32, 42 adjacent the portion of the principal communication zone 32 having a first indicium 26 associated with the first consumer product 16. The second product offering indicium 176 is located on a communication zone 43 adjacent the portion of the principal communication zone 32 having a second indicium 28 associated with the second consumer product 18.

A count indicium 175 is provided on a package to describe the amount of product(s) at least partially contained within the package. In packages at least partially containing at least two different consumer products, a first count indicium 175 associated with the first consumer product 16 and a second count indicium 177 associated with the second consumer product 18 are provided. The first count indicium 175 and the second count indicium 177 are located in the bottom of the communication zone 42, preferably the bottom half 130 of the communication zone 42, or more preferably in the bottom third 132 of the communication zone, or most preferably in the bottom-most portion 134 of the communication zone (i.e. along the bottom-most edge of the communication zone. Preferably, the count indicium 175 is at least on the principal communication zone 30. In embodiments having, a first count indicium 175 associated with the first product 16 and a second count indicium 177 associated with the second product 18, the first count indicium 175 and the second count indicium 177 are provided such that they are symmetrically located on the principal communication zone 32. In other embodiments, other quantitative indicium such as but not limited to: absorbency, size, age, or stage, are provided. One skilled in the art understands that the present disclosure is not limited to the embodiments explicitly described.

A fragrance indicium 182 can be provided to describe a consumer product that has a scent or is unscented. The fragrance indicium 182 can be a visual indicium and/or olfactory. In some embodiments, the fragrance indicium 182 is a caricature, picture and/or photograph of the scent that is included in the consumer product and/or synthetically emulated on or in the consumer product. The fragrance indicium 182 may require interaction from a consumer and thus be a tactile indicium. As described throughout the present disclosure, a fragrance indicium 182 can be located in a plurality of different places on or within a package.

In some embodiments of the present disclosure, various indicia 25 have a specific visual, tactile, olfactory and/or audible indicium. The specific features of the indicium 25 (i.e. color, texture, pattern, font, scent, reverberation, etc. . . . ) as applied to the forefront 178 and/or background 180 aspects of the indicium 25, and/or the location of the indicium can be systematic amongst a product scheme and/or a packaging scheme of one or more consumer products. This can be advantageous as the consumer is more likely to find types of information and specific information about a consumer product quickly and easily.

A product regulatory indicium 184 can be provided as required for some consumer products. Product regulatory indicium 184 can include mandatory warnings as required by a government body (i.e. TSS warnings, choking hazard warnings, flammability warnings, etc. . . . ) other recommended warnings or notices, and/or any other warnings or notices that a seller or manufacturer may deem necessary to ensure proper usage of the consumer product. A product regulatory indicium 184 can also include mandatory product information such as but not limited to: country of origin, absorbency, size, ingredients, inactive ingredients, or active ingredients. As such, one or more product regulatory indicium 184 may be required on a single package that at least partially contains one or more consumer products. In some embodiments, a product regulatory indicium 184 is provided on an exterior surface 20, an interior surface 20, and/or on a packaging structure 144. In some embodiments, a product regulatory indicium 184 is placed in the interior 21 of the package amongst the product(s) at least partially contained within the package.

Figure 20:
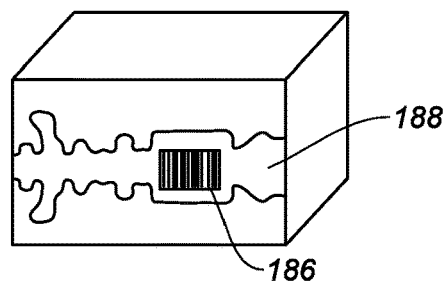
FIG. 20 is a representation of an embodiment of an indicium

Referring to the embodiment shown in FIG. 20, a scannable code indicium 186 can be provided. A scannable code indicium 186 such as a UPC, QR code, unique device identifier ("UDI"), and/or other scannable codes can provide information to the manufacturer as the package is being made/packaged, to a distributer and/or retailer of a product. A scannable code indicium 186 may also provide information to consumers and/or to a government body about the consumer product. In some instances, a scannable code indicium is also a product regulatory indicium 184 (i.e. a UDI). Scannable code indicium 186 tends to be consistent amongst consumer products, but in some embodiments, it is further leveraged by drawing further similarities and/or differences amongst consumer products.

A printing machine indicium 188 is typically a stripe of packaging material about a periphery and/or seam of the package. A printing machine indicium 188 is often-times white, black or having a plain appearance as is required by the machine creating and/or assembling the package, packaging material and/or packaging aesthetics. In some embodiments, a printing machine indicium 188 is embellished to make a further aesthetically pleasing package. This alleviates a detracting feature on prior art packages and makes it synergistic with the indicium, packaging scheme and/or product scheme of the present disclosure. In further embodiments, a printing machine indicium 188 creates a texture, tessellation and/or pattern that extends into at least one other indicium 25 on a package. In some embodiments, this other indicium 25 has a background or forefront that merges with the printing machine indicium. In some embodiments, the printing machine indicium 188 and a scannable code indicium 186 are associated with each other via a texture, tessellation and/or pattern extending from the printing machine indicium 188.

Figure 21:
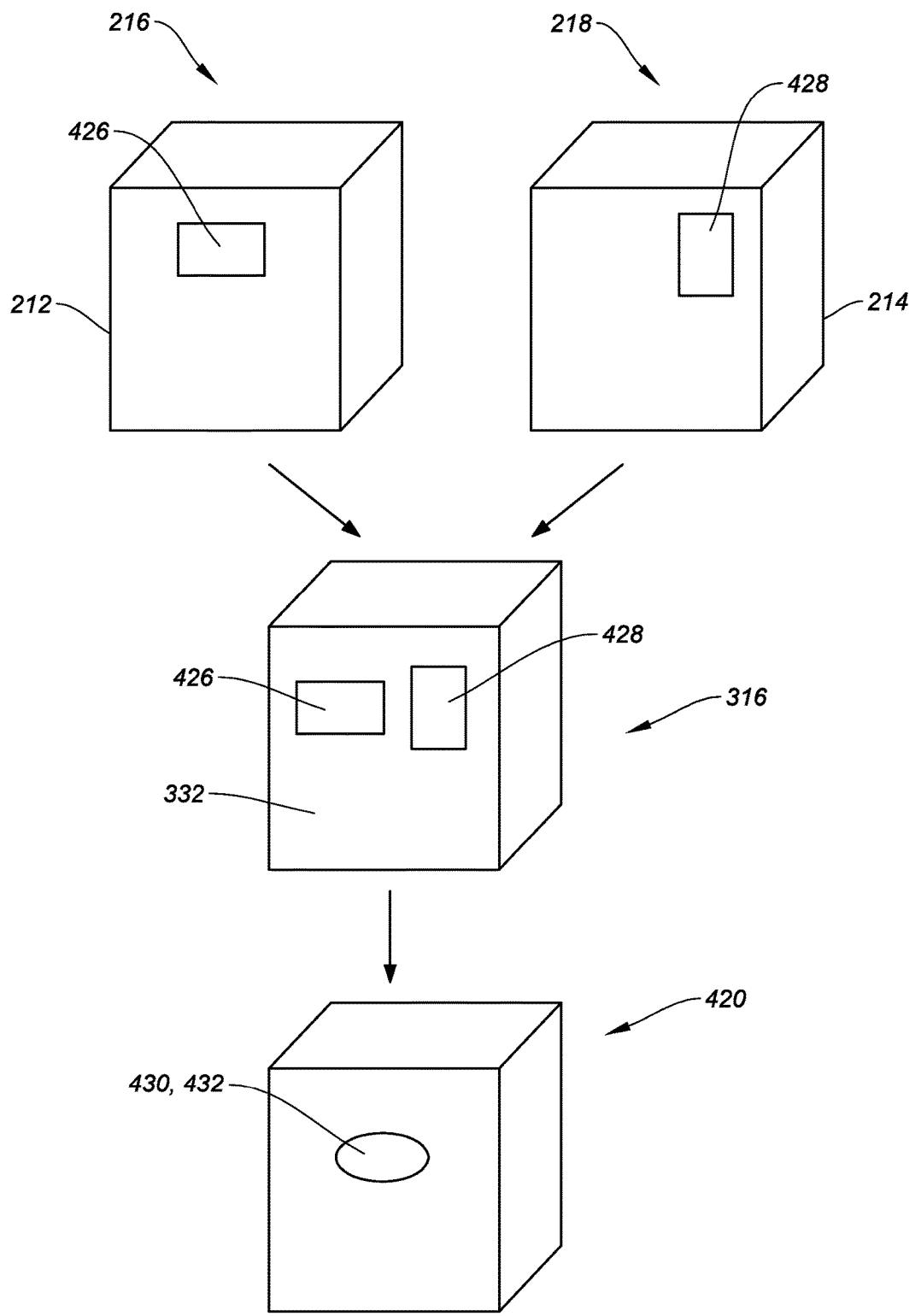
FIG. 21 is a representation of an embodiment of a packaging scheme for two merged products

Referring to the embodiment shown in FIG. 21, a packaging scheme for two product lines being merged 190 into one product line is provided. A first product line 216 has at least one first key product indicium 426 on a first package 212. A second product line 218 has at least one second key product indicium 428 on a second package 224. A new product line 316 has, initially, has at least both a first key product indicium 426 and a second key product indicium 428 located on the principal communication zone 332 of the new package 312. After a substantial period of time enabling a significant number of consumers to recognize the merging of the first product line 216 and the second product line 218, the at least one first key product indicium 426 and the at least one second key product indicium 428 on the new package 312 are blended to create a third key product indicium 430. The third key product indicium 430 becomes the new key product indicium 432 going forward for the new product line 420. This packaging scheme 190 is particularly useful for merging two product lines that are resultantly manufactured or sold by one company due to a merger and/or acquisition. In some embodiments, the first product line 216 and the second product line 218 were direct competitors that each had at least one marketable advantage over the other. In some embodiments, the first key product indicium 426 and/or the second key product indicium 428 are associated with the marketable advantage.

In other embodiments, merger and acquisition leads to adjacent and/or related consumer products being made and/or sold by one company. In this scenario, a first key brand, sub-brand and/or master brand indicium 426 from a first product line 216 and a second key brand, sub-brand and/or master brand indicium 428 from a second product line 218 may be merged to describe a new key product line brand, sub-brand and/or master brand indicium 432. In other embodiments, the first key brand, sub-brand and/or master brand indicium 426 may be applied to a first package 12 at least partially containing at least the first product line 216 and the second product line 218 such that the first key brand, sub-brand and/or master brand indicium 426 on the first package 12 describes both the first product line 216 and the second product line 218.

Figure 22:
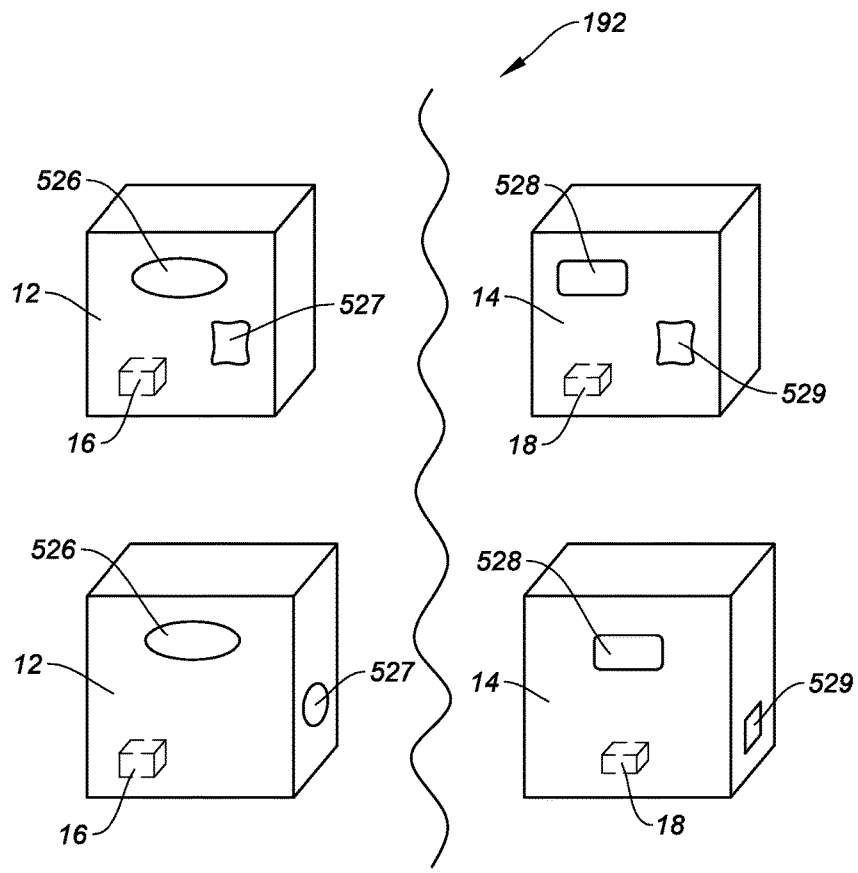
FIG. 22 is a representation of an embodiment of a multi-jurisdictional packaging scheme

Referring to the embodiment shown in FIG. 22, A multi-jurisdictional packaging scheme 192 is also provided. A first package 12 of a first consumer product 16 is sold in a first region, having a first indicium 526 and optionally a second indicium 527. A second package 14 of a second consumer product 18 is sold in a second region, having a third indicium 528 and optionally a fourth indicium 529. The first consumer product 16 is similar to the second consumer product 18. The first indicium 526 is similar to the third indicium 528. The second indicium 527 is different from the fourth indicium 529. The first indicium 526 and the third indicium 528 are similar such that a consumer in either region, upon travelling to the other region, would understand that the first consumer product 16 and the second consumer product 18 are similar and/or are made and/or sold by the same company. The second indicium 527 and fourth indicium 529 are not similar in that they each convey information differently to target the needs and/or concerns of a particular consumer in a particular region. In one embodiment, the first indicium 526 and third indicium 528 are a brand, sub-brand and/or master brand indicium. In another embodiment, the first indicium 526 and the third indicium 528 are a visual and/or tactile indicium such as the same first predominant color 226. In yet further embodiments, the second indicium 527 and the fourth indicium 529 are each a different brand, sub-brand and/or master brand indicium. One skilled in the art understands that other types of indicium such as visual and/or packaging structure indicium are within the scope of the present disclosure. One skilled in the art further understands that (i) a third package, fourth package, nth package, (ii) a third region, fourth region, nth region, and/or (iii) a fifth indicium, sixth indicium, nth indicium, are all within the scope of the present disclosure.

Figure 23:
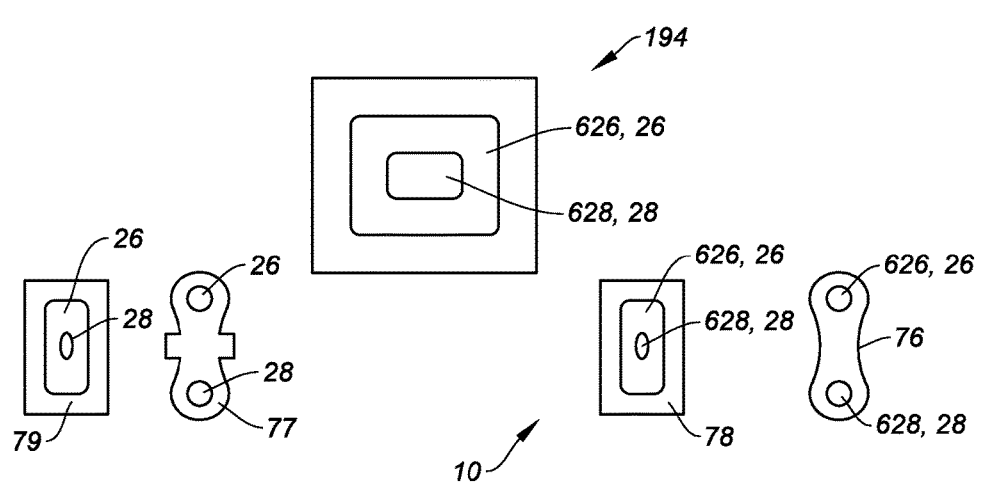
FIG. 23 is a representation of an embodiment of a packaging scheme
Figure 24:
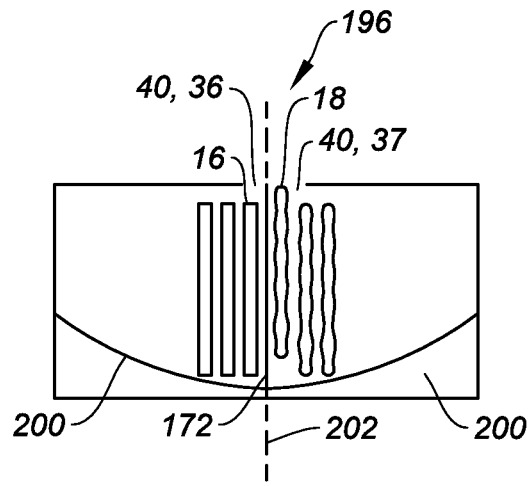
FIG. 24 is a representation of an embodiment of a packaging scheme
Figure 25:
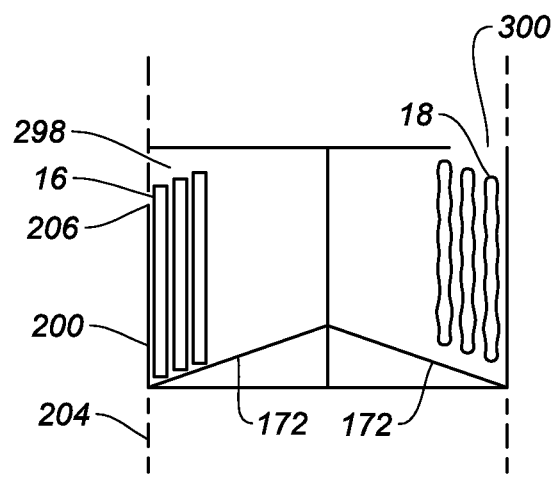
FIG. 25 is a representation of an embodiment of a packaging scheme
Figure 26:
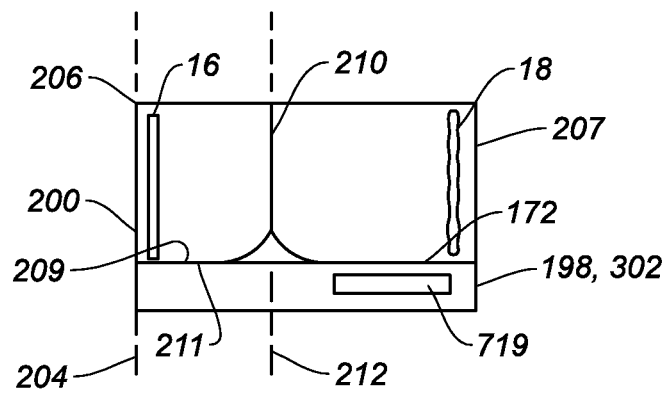
FIG. 26 is a representation of an embodiment of a packaging scheme
Figure 27:
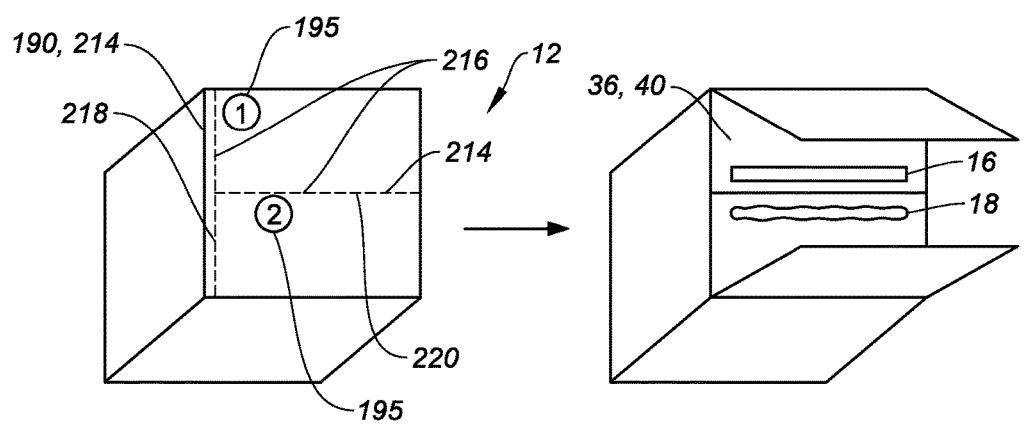
FIG. 27 is a representation of an embodiment of a package
Figure 28:
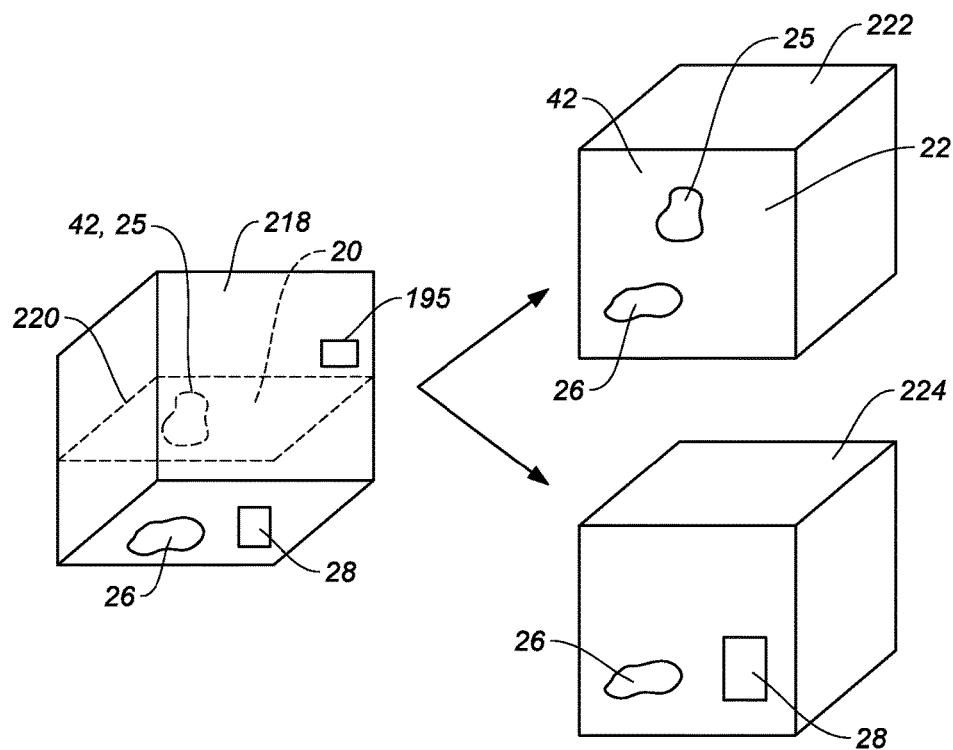
FIG. 28 is a representation of an embodiment of a package

Referring to the embodiment shown in FIG. 23, a digital packaging scheme 194 is also provided but is not so limited to just digital and/or electronic retail. The digital packaging scheme 194 simplifies the information provided to the consumer by at least one of (i) maximizing the size of the indicium on the product package that is associated with the consumer product and/or (ii) simplifying the information provided by the indicium on the consumer product package that is associated with the product such that a consumer can quickly identify the consumer product from the indicium 25 in what may be a tiny and/or confined image of the consumer product package. In view of a multitude of consumer products, simplifying the information provided by the indicium 25 associated with the consumer product can be challenging in that the indicium 25 has to be distinct and recognizable as being associated with the specific consumer product. As such, and in light of being easily identified via digital and/or electronic retail, the indicium 25 is a visual cue and/or a packaging structure cue, such as a visual indicium. The visual indicium may be an aesthetic indicium such as a color and/or pattern. The visual indicium may be a caricature, cartoon, picture, photo, rendering, image and/or silhouette. The visual indicium may also be a brand, a sub-brand and/or a master brand. In one embodiment, a first visual indicium 626 and a second visual indicium 628 are provided in concert such that the first visual indicium 626 and the second visual indicium 628 can be perceived harmoniously in a small electronic and/or digital image. In one embodiment, the first visual indicium 626 is a predominant background and/or foreground color and/or pattern. In another embodiment, the second visual indicium 628 is a brand, sub-brand and/or master-brand indicium.

In a further embodiment, the digital packaging scheme is applied to the consumer product 76 and/or the product wrapper 78. In other words, the package, the consumer product 76 and/or the consumer product wrapper 78 all have the same a first indicium 26 and optionally the same second indicium 28. This embodiment is preferable where multiple product images and/or views are available via electronic and/or digital retail.

In some embodiments, the packaging scheme 10 is enhanced by having the wrapper(s) of the product(s) within the package also have at least one indicium that is in common with the package. In one embodiment, a package has at least two different consumer products. The package has a principal communication zone 30 with at least a first indicium 26 that is associated with a first consumer product 76 and at least a second indicium 28 associated with a second consumer product 28. The first consumer product 26 has a first wrapper 78 having at least a first indicium 26. The second consumer product 77 has a second indicium 79 having at least a second indicium 28. These embodiments are preferable such that the consumer is consistently reminded throughout at least two interactions with the package and the product of the indicium that is associated with the product.

In some embodiments, the packaging scheme 10 is enhanced by having the product(s) within the package also having at least one indicium that is in common with the package. In one embodiment, a package has at least two different consumer products. The package has a principal communication zone with at least a first indicium 26 that is associated with a first consumer product 16 and at least a second indicium 28 associated with a second consumer product 18. The first consumer product 16 has at least a first indicium 26. The second consumer product 18 has at least a second indicium 18. These embodiments are preferable such that the consumer is consistently reminded throughout at least two interactions with the package and the product of the indicium that is associated with the product.

In some embodiments, a packaging construction cue 196 can improve how the package and consumer product(s) contained therein interact with the consumer. In one embodiment, a packaging construction cue 196 enables a consumer to understand how to open the package and/or actually open the package more quickly and/or more easily. In some embodiments having at least two consumer products, the packaging construction cue 196 enables a consumer to be able to particularly and/or easily locate where a particular consumer product 16 is within the package and/or be able to easily remove the particular consumer product 16 from the package 12. In further embodiments, the at least two consumer products are different but related consumer products. In some embodiments, a packaging construction cue 196 provides a port 36 such as an opening 40 that enables the consumer to remove at least one consumer product 16. In further embodiments, at least two packaging construction cues 196, 198 are available, each providing a separate port 36, 37 that enables a consumer to more precisely (than prior art containers having a single port) remove a different related consumer product 16, 18 from each port 36, 37, respectively.

In yet further embodiments, a packaging structure 172, in combination with a packaging construction cue 196 enable a consumer to more easily interact with the package and the consumer product(s) contained therein. In one embodiment, a first packaging structure 172 separates at least two consumer products within a package. The first packaging structure 172 defines an axis 202. The first packaging construction cue provides a port such as an opening such that upon opening the package, a consumer readily understands that at least two consumer products are separated by the first packaging structure 172. In this embodiment, a consumer may be easily able to select both consumer products about the first packaging structure 172 and remove both consumer products in a single motion, with a single hand.

In a further embodiment, a second packaging structure 200 is provided to further assist a consumer in removing consumer products from within a package. In this embodiment, the second packaging structure 200 is provided on a bottom-side of the package (i.e. at least in a use state; the bottom-side being generally parallel to and adjacent the ground and/or a level surface on which the package rests). The second packaging structure 200 provides at least an interior bottom surface that has a slope directing product on either side of the packaging structure such that as consumer products closer to the first packaging structure are removed, the remaining consumer products move (i.e. slide and/or shift) towards the first packaging structure in the space vacated by the removed consumer products. In this fashion, the first packaging structure 172 and the second packaging structure 200 operate symbiotically to facilitate the consumer's repeated ease of removing consumer products from the package. In some embodiments, the second packaging structure 200 is concave, curved and/or has a two negative linear slopes that approach the first packaging structure 172 as defined by the axis 202 of the first packaging structure 172.

In other embodiments, it may be preferable to direct product out of a port 298 that is situated towards a peripheral edge 206. In this embodiment, a first packaging structure 172 is provided on a bottom-side of the package (i.e. at least in a use state; the bottom-side being generally parallel to and adjacent the ground and/or a level surface on which the package rests). A second packaging structure 200 that provides the peripheral edge 206 defines an axis 204. The first packaging structure 172 provides at least an interior bottom surface that has a slope directing product to the port 298 on the peripheral edge 204 of the package such that as consumer product(s) closer to the peripheral edge 206 is(are) removed, the remaining consumer product(s) move(s) (i.e. slide and/or shift) toward(s) the first packaging structure 172 in the space vacated by the removed consumer product(s). In other words, the first packaging structure 172 has a negative slope as it approaches the axis 204 defined by the second packaging structure 200 giving rise to the peripheral edge 206. This is preferable for a consumer having limited space to store the package and thus reduces the space needed to remove product from the package.

In some embodiments, at least one first consumer product 16 and at least one second consumer product 18 are separated by a first packaging structure 172. The at least one first consumer product 16 is accessible and/or removable from a first port 298. The least one second consumer product 18 is accessible and/or removable from a second port 300. The first port 298 and the second 300 port can be aligned such that the consumer can remove both the least one first consumer product 16 and the least one second consumer product 18 in one action and/or with one hand.

Alternatively, in embodiments where it is desirable to remove only one consumer product at a time, the first port and the second port may be positioned such that accessing one port won't agitate the second port and thus cause accidental removal or spillage from the other port.

In some embodiments, a third packaging structure 210 is provided to further assist a consumer in removing consumer products from within a package. The third packaging structure 210 separates at least two consumer products within a package. The third packaging structure 210 defines an axis 212. The first packaging structure 172 provides at least an interior bottom surface that has a slope directing product toward the peripheral edge 206 (i.e. away from the third packaging structure) such that as consumer product(s) closer to the peripheral edge 206 is(are) removed, the remaining consumer product(s) move(s) (i.e. slide and/or shift) toward(s) the peripheral edge 206 in the space vacated by the removed consumer product(s). This embodiment may be preferable for a consumer who can easily access a peripheral edge 206 of the package but not directly access and/or remove product from a central region of the package near the third packaging structure 212. This embodiment may also be preferable for packages having at least two different related consumer products that are used in series, such that a first consumer product 16 can be accessed and removed from a first peripheral edge 206, perhaps until all of that first consumer product 16 is exhausted, and then the second consumer product 18 can be accessed and removed from a second peripheral edge 207, perhaps until all of that second consumer product 18 is exhausted. In this embodiment, the package can be rotated such that a second peripheral edge 207 is the most convenient edge to access and/or remove product from.

In further embodiments, a third different but related consumer product 719 is provided in the package. In embodiment, the third consumer product 719 may be situated within the package such that any dead-space created by a sloped interior bottom surface can be utilized. In other words, the sloped interior bottom surface has a top surface 209 and a bottom surface 211, the bottom surface 211 is adjacent the third consumer product 719. This embodiment is preferable from a slack-fill vantage point such that the consumer is not misled to believe the entire package is filled with product(s) despite a voided space that is not immediately obvious to the consumer. In this embodiment the third consumer product 719 can be removable from the same port 36 as either the first consumer product 16 and/or second consumer product 18. In some embodiments, the packaging structure 172 providing the sloped interior bottom surface is at least partially movable and/or at least partially removable from the package such that the third consumer product 719 can be accessed. In other embodiments, an additional packaging construction cue 198 is provided such that the consumer can located and/or open a 302 port to access the third consumer product 719 separately from the first consumer product and/or second consumer product.

In some embodiments, the sloped interior bottom surface can be synergistic with a port 36. In one embodiment, at least one first consumer product 16 is disposed within a first package 12 such that (a) the at least one first consumer product 16 is positioned near the port 36, or (b) the at least one first consumer product 16 travels along the interior bottom surface to the port 36 for easy access and/or removal. In this manner, utilizing the orientation of the first consumer product 16 within the first package 12, the weight of the at least one first consumer product 16 (i.e. gravity's pull on the mass of the at least one first consumer product towards the lowest point of the interior bottom surface in relation to the ground/horizontal surface on which the first package 12 rests), the slope of the sloped interior bottom surface, and/or the frictional coefficient of the sloped interior bottom surface, the at least one consumer product 16 is queued towards the port 36. In likewise manner, other consumer products will travel towards the space vacated by the first consumer product 16 for subsequent easy access and/or removal.

As shown in the embodiment of FIG. 31, a package structure in the interior of the package is provided such that a first product is positioned in a manner that is easier to access and/or remove than any other product within the package. In such embodiments, at least a portion of the package is made of a molded material such as molded pulp that assists in elevating and/or making at least one of such first product more accessible and/or easier to remove.

In further embodiments a packaging structure can use multiple materials to assist in showcasing at least one of a product to a consumer. For instance, a packaging structure that is a molded material can orient at least one product such that it is perpendicular, angled, parallel and/or skew to at least another product, and/or is separate from at least one other product. In some such embodiments a second packaging structure enables this at least one product to be at least partially visible without removing such at least one product.

In further embodiments, the packaging structure not only assists in showcasing the at least one product, but also positions the at least one product in a manner that enables easier access and/or removal of the product.

In some embodiments, a first consumer product 76 is a tampon, a second consumer product is a napkin such as a liner or a pad, and a third consumer product is a personal cleansing cloth. In another embodiment, a first consumer product is a tampon, a second consumer product is a napkin, and a third consumer product is an incontinence device. In another embodiment, a first consumer product is a razor, a second consumer product is a shaving preparation, and a third consumer product is a post-shaving treatment such as a lotion. One skilled in the art understands many permutations and combinations of related consumer products exist.

In some embodiments, the packaging construction cue 196 is a perforation 214. For purposes of the present disclosure, the terms "perforation", "line of weakness", "slitted" and other similar terms are synonymous and all describe a feature that the consumer can apply a force to in order to create at least partial separation amongst the feature. In other words, a perforation 214 enables a consumer to take a feature and at least partially separate, tear, rupture and/or create an opening within the feature.

In some embodiments, a perforation 214 is a step-wise perforation 216 such that a series of perforations 214 are performed in sequence. In some embodiments, the stepwise perforations 216 are connected and/or are adjacent each other such that completion of a first step 218 can be continuous (or nearly continuous) and/or cue the second step 220. In some embodiments, the stepwise perforations 216 are at different angles to each other thus requiring the consumer to change directions upon completion of a first step 218. In further embodiments, the step-wise perforation 214 has at least one visual cue 195 and/or packaging construction cue 196 to assist the consumer in identifying the start of the step-wise perforation 214 and/or propagating the perforation 214. In other embodiments further visual cues 195 and/or packaging construction cues 196 are provided such that the further steps in the perforation 214 are understood and executed. Optionally the further visual cues 195 and/or packaging construction cues 196 are provided such that the consumer executes the steps in the proper order.

In further embodiments, a step-wise perforation 216 permits the formation of a port 36 such as an opening 40 revealing, in series, a first consumer product 16 and then a second consumer product 18. In some embodiments, the first consumer product 16 and second consumer product 18 are different but related consumer products. In further embodiments, the step-wise perforation 216 permits fragmentation of the package 12 into one or more sub-packages 222. In this embodiment, the one or more sub-packages 222 can further protect the consumer product 76 contained therein such that (i) the consumer product does not need a further wrapper, (ii) the consumer product has further protection during its transport in a more portable state, and/or (iii) the consumer product 76 is easier to store individually than in a group of at least two consumer products. In further embodiments, the one or more sub-packages 222 all have at least one indicium 26 that is the same such that it is clear to the consumer that each of the one or more sub-packages 222 are from the same initial package 12.

Other means of initially maintaining a package 12 in a unitary state and thereafter permitting separation of the package into at least one sub-package 222 comprise, without limitation: adhesives, tape, stickers, mechanical fasteners such as clips, staples, elastomeric bands, and heat sealing.

Referring to the embodiments shown in FIGS. 27-30, a first package 12 at least partially contains at least one sub-package 222. The at least one sub-package 222 is accessible via a port 36. In some embodiments, the port 36 has a latch or a lock mechanism 226 that allows selective disengagement and/or re-engagement.

In some embodiments, the package 12, sub-package 222 and/or wrapper 78 are made from a water-impervious material such as a laminate, a plastic and/or an elastomeric material. The interior surface and/or exterior surface can be water-impervious. In some embodiments, the package, sub-package and/or wrapper are made from a material that is pleasing to touch (i.e. a soft, plush, textured and/or smooth material). The interior surface and/or exterior surface can be pleasing to touch in at least some parts. In other embodiments, the package, sub-package and/or wrapper are made from other known materials and/or layers of materials such as laminates, films, foils, molded materials, paper and/or pulp materials such as cardboard, card-stock and molded pulp, plastics that are flexible and/or rigid, wood, sheet metal, and/or combinations thereof.

In some embodiments, a package 12 at least partially contains at least two different but related consumer products. In these embodiments, the package 12 may also be fragmentable by an attachment means such as a perforation 214 (and optionally a step-wise perforation 216) such that a first sub-package 222 at least partially contains a first consumer product 16 and a second sub-package 224 at least partially contains a second consumer product 18. A further embodiment is provided such that a first sub-package 222 at least partially contains at least a first consumer product 16 and at least a second consumer product 18. This embodiment is preferable for a consumer that would like to have quick access to two related consumer products that are to be used in parallel and/or in quick succession. This may also be preferable for retailers that have varying retail space in various retail outlets, such that the retailer can modify the size of the package sold (this would likely require regulatory indicium 184 on each sub-package). In these embodiments, a first indicium 26 may correlate to a first consumer product 16 and a second indicium 28 may correlate to a second consumer product 18. In these embodiments, the first indicium 26 would be on any sub-packages 222 at least partially containing a first consumer product 16. In these embodiments, a second indicium 28 would be on any sub-package 224 at least partially containing a second consumer product 18.

In embodiments that permit separation into one-or more sub-packages 222, surfaces that were initially interior surfaces 22 (and/or packaging structures 172) might now be exterior surfaces 20. As such, multiple communication zones 42 may be newly recognizable upon creating each sub-package 222 and thus may provide further information via further indicium 25. Alternatively, further communication zones 42 may provide similar information via similar indicium 25 as on the package prior to creating at least one sub-package 222.

In some embodiments, a first package 12 contains a quantitative indicium 726 and a second package 14 contains a second quantitative indicium 728. The first quantitative indicium 726 is different from the second quantitative indicium 728 but describe the same attribute for each package. As such, one or more geometric parameters may be different and thus the first package 12 may have a different size and/or shape than the second package 14. In some such embodiments, at least one of any indicium 26 on the first package 12 and at least one of any indicium 28 on a second package 14 are located in at least one of a proportional and/or geographically similar manner. The same rationale can be applied to a first package 12 and at least one sub-package 222.

In some embodiments, a package has at least two consumer products where each consumer product is located at an end of the package. The package comprises a first packaging structure 200 at a first end 226 that enables easy access to and/or removal of at least the first consumer product 16, and a second packaging structure 210 at a second end 228 that enables easy access to and/or removal of at least the second consumer product 18. In this embodiment, the first packaging structure 200 and/or second packaging structure 210 have a perforation 214. These embodiments may be preferable for a consumer with limited space to access and/or remove products and thus enable the consumer to flip the package from a first side 230 to a second side 232 to more easily access the product(s) within the package.

In an alternative embodiment, a packaging structure 172 provides the consumer the ability to create a port 36 such as an opening 40 by completely removing a surface and/or panel of the package. By completely removing a surface and/or panel of the package, the consumer is able to more easily access and/or remove the product(s) from the package by avoiding having to pass-by the surface and/or panel still at least partially connected to the package and/or having to push the surface and/or panel aside such that the product(s) within the package can be accessed and/or removed. In some embodiments, the packaging structure 172 has a perforation 214.

Although the present disclosure has been described and illustrated with reference to specific exemplary embodiments thereof, it is not intended that the invention be limited to those exemplary embodiments. Those skilled in the art will recognize that variations and modifications can be made without departing from the true scope of the present disclosure as defined by the claims that follow. For instance, features disclosed in connection with any one embodiment can be used alone or in combination with each feature of the respective other embodiments.

What is claimed is:
1. A plurality of related consumer products at least partially contained in at least two packages comprising:
 a first consumer package at least partially containing a first consumer product, said first package having at least a first principal communication zone having a first indicium;
 a second consumer package at least partially containing said first consumer product and a second consumer product, said second consumer package having at least a second principal communication zone having said first indicium and a second indicium;
 wherein said first indicium is associated with said first consumer product and said second indicium is associated with said second consumer product, where said second consumer product is different from said first consumer product,
 wherein said first consumer product is a tampon, and the second consumer product is one of a wipe and a feminine care napkin,
 wherein said first consumer package and said second consumer package have a product scheme and a packaging scheme, wherein said first indicium is one of a first visual cue and a first packaging structure cue; and wherein said second indicium is one of a second visual cue and a second packaging structure cue.

2. The plurality of related consumer products of claim 1, further comprising a third consumer package at least partially containing said second consumer product, said third consumer package having a third principal communication zone having said second indicium.

3. The plurality of related consumer products of claim 1, wherein said second principal communication zone has symmetry with respect to said first indicium and said second indicium.

4. The plurality of related consumer products of claim 1, wherein said first indicium comprises a first quantitative indicium about said first consumer product, and said second indicium comprises a second quantitative indicium about said second consumer product.

5. The plurality of related consumer products of claim 4, wherein said first indicium and said second indicium are proportionally sized within said second principal communication zone based on the first quantitative indicium and second quantitative indicium.

6. The plurality of related consumer products of claim 1, wherein said first indicium and said second indicium on said second principal communication zone are proportional to the volume of said first consumer product and said second consumer product within said second package, respectively.

7. The plurality of related consumer products of claim 1, wherein said second consumer package has an exterior surface opposite an interior surface, wherein said second consumer package comprises at least one of a port and/or an at least partially translucent portion of said exterior surface such that at least one of said first consumer product is at least partially visible.

8. The plurality of related consumer products of claim 7, wherein at least one of said second consumer product and/or a wrapper of said second consumer product is at least partially visible.

9. The plurality of related consumer products of claim 7, wherein said second consumer package has at least two ports and/or at least partially translucent portions of said exterior surface.

10. The plurality of related consumer products of claim 1, wherein said first consumer package and said second consumer package each have a swoosh.

11. The plurality of related consumer products of claim 1, wherein said first indicium on said second consumer package is proportional to the first consumer product contained within said second consumer package.

12. The plurality of related consumer products of claim 1, wherein said second consumer package comprises a visual indicium such as at least two silhouettes, wherein a first silhouette corresponds to said first consumer product and has a first aesthetic, and a second silhouette corresponds to a second consumer product and has a second aesthetic.

13. The plurality of related consumer products of claim 12, wherein said first consumer package comprises a visual indicium comprising at least one silhouette, wherein said first silhouette corresponds to said first consumer product and said first silhouette has a first aesthetic on said first consumer package.

14. The plurality of related consumer products of claim 12, wherein said first silhouette is positioned on said second package such that said first silhouette is at least partially on a first principal communication zone and a second adjacent communication zone.

15. The plurality of related consumer products of claim 1, wherein said second package has a perforation.

16. The plurality of related consumer products of claim 1, wherein said second package is separable into at least two sub-packages, wherein a first sub-package and a second sub-package are connectable by attachment means.

17. The plurality of related consumer products of claim 16, wherein at least one of said sub-packages comprises at least one of said first consumer product and at least one of said second consumer product.

18. The plurality of related consumer products of claim 1, wherein at least one of said first consumer product and said second consumer product is more accessible than the remaining first and second consumer products.

19. The plurality of related consumer products of claim 1, wherein said second consumer package permits removal of said first consumer product and said second consumer product with one hand.

* * * * *